(12) United States Patent
Popik et al.

(10) Patent No.: US 8,912,322 B2
(45) Date of Patent: Dec. 16, 2014

(54) AZA-DIBENZOCYCLOOCTYNES AND METHODS OF MAKING AND USING SAME

(75) Inventors: Vladimir V. Popik, Watkinsville, GA (US); Alexander Kuzmin, Tucson, AZ (US); Andrei Polukhtine, Scottsdale, AZ (US)

(73) Assignee: University of Georgia Research Foundation, Inc., Athens, GA (US)

( * ) Notice: Subject to any disclaimer, the term of this patent is extended or adjusted under 35 U.S.C. 154(b) by 371 days.

(21) Appl. No.: 13/187,643

(22) Filed: Jul. 21, 2011

(65) Prior Publication Data

US 2012/0029186 A1 Feb. 2, 2012
US 2012/0197012 A9 Aug. 2, 2012

Related U.S. Application Data

(60) Provisional application No. 61/368,775, filed on Jul. 29, 2010.

(51) Int. Cl.
C07D 225/08 (2006.01)
C07D 487/04 (2006.01)

(52) U.S. Cl.
CPC ............ *C07D 225/08* (2013.01); *C07D 487/04* (2013.01)
USPC ....................................................... 540/479

(58) Field of Classification Search
None
See application file for complete search history.

(56) References Cited

U.S. PATENT DOCUMENTS

| | | | |
|---|---|---|---|
| 8,133,515 | B2 | 3/2012 | Boons et al. |
| 8,258,347 | B2 | 9/2012 | Popik et al. |
| 8,426,649 | B2 | 4/2013 | Popik et al. |
| 2012/0208722 | A1 | 8/2012 | Dluhy et al. |
| 2012/0295318 | A1 | 11/2012 | Popik et al. |
| 2012/0322974 | A9 | 12/2012 | Boons et al. |

FOREIGN PATENT DOCUMENTS

| | | |
|---|---|---|
| WO | 2009/053339 A2 | 4/2009 |
| WO | 2009/067663 A1 | 5/2009 |

OTHER PUBLICATIONS

Ning. Bioorthogonal Reactions, 2010, 49, 3065-68.*
Agard et al. "A Strain-Promoted [3+2] Azide-Alkyne Cycloaddition for Covalent Modification of Biomolecules in Living Systems" 2004. *J. Am. Chem. Soc.* 126:15046-15047.
Agard et al. "A Comparative Study of Bioorthogonal Reactions with Azides" 2006. *ACS Chem. Biol.* 1(10):644-648.
Bantscheff et al. "Quantiative mass spectrometry in proteomics: a critical review" 2007. *Anal. Bioanal. Chem.* 389:1017-1031.
U.S. Appl. No. 13/876,024, filed Mar. 26, 2013, Boons.
Baskin et al. "Bioorthogonal Click Chemistry: Covalent Labeling in Living Systems" 2007. *QSAR Comb. Sci.* 26:1211-1219.
Baskin et al. "Copper-free click chemistry for dynamic in vivo imaging" 2007. *Proc. Natl. Acad. Sci. U.S.A.* 104(43):16793-16797.
Becer et al. "Click Chemistry beyond Metal-;Catalyzed Cycloaddition" 2009. Angew. Chem. Int. Ed. 48:4900-4908.
Bernardin et al. "Copper-Free Click Chemistry for Highly Luminescent Quantum Dot Conjugates: Application to in Vivo Metabolic Imaging" 2010. *Bioconjugate Chem.* 21:583-588.
Binder et al. "Click Chemistry in Polymer and Material Science: An Update" 2008. *Macromol. Rapid Commun.* 29:952-981.
Bottcher et al. "Showdomycin as a Versatile Chemical Tool for the Detection of Pathogenesis-Associated Enzymes in Bacteria" 2010. *J. Am. Chem. Soc.* 132:6964-6972.
Burrows et al. "Oxidative Nucleobase Modifications Leading to Strand Scission" 1998. *Chem. Rev.* 98:1109-1152.
Canalle et al. "Copper-Free Clickable Coatings". 2009. *Adv. Funct. Mater.* 19:3464-3470.
Chaffins et al. "An Efficient Synthesis of Dibenzocycloocta-4a,6a,-diene-5,11-diyne and its precursors" 2002. *Synthesis.* 1191-1194.
Chang et al. "Copper-free click chemistry in living animals" 2010. *Proc. Nat. Acad. Sci.* 107(5):1821-1826.
Chin et al. "An Expanded Eukaryotic Genetic Code" 2003. *Science.* 301(5635):964-967.
Choi et al. "Surface Modification of Functional Nanoparticles for controlled Drug Delivery" 2003. *J. Dispersion Sci. Tech.* 24(3,4):475-487.
Clark et al. "Rearrangement of ammonium ylides produced by intramolecular reaction of catalytically generated metal carbenoids. Part 1. Synthesis of cyclic amines" 2001. *J. Chem. Soc. Perkin Trans.* 1:3312-3324.
Codelli et al. "Second-Generation Difluorinated Cyclooctynes for Copper-Free Click Chemistry" 2008. *J. Am. Chem. Soc.* 130:11486-11493.
Debets et al. "Aza-dibenzocyclooctynes for fast and efficient enzyme PEGylation via copper-free ((3+2) cycloaddition" 2010. *Chem. Commun.* 46:97-99.
Debets et al. "Azide: A Unique Dipole for Metal-Free Bioorthogonal Ligations" 2010. *ChemBioChem.* 11:1168-1184.
Dedola et al. "Recent applications of the CUI-catalysed Huisgen azide-alkyne 1,3-dipolar cycloaddition reaction in carbohydrate chemistry" 2007. *Org. Biomol. Chem.* 5:1006-1017.
Dicken et al. "Reactions at High Pressures. [3+2] Dipolar Cycloaddition of Nitrones with Vinyl Ethers" 1982. *J. Org. Chem.* 47(11):2047-2051.

(Continued)

*Primary Examiner* — Noble Jarrell
(74) *Attorney, Agent, or Firm* — Mueting Raasch & Gebhardt, P.A.

(57) ABSTRACT

Convenient methods of preparing aza-dibenzocyclooctynes are disclosed herein. Aza-dibenzocyclooctynes attached to a surface are also disclosed herein. Aza-dibenzocyclooctynes can be reacted with azides to form heterocyclic compounds. Such reactions can be useful in a wide variety of applications including, for example, labeling surfaces.

17 Claims, 10 Drawing Sheets

(56) References Cited

OTHER PUBLICATIONS

Ess et al. "Transition States of Strain-Promoted Metal-Free Click Chemistry: 1,3-Dipolar Cycloadditions of Phenyl Azide and Cyclooctynes" 2008. *Org. Lett.* 10(8):1633-1636.

Fernandez-Suarez et al. "Redirecting lipoic acid ligase for cell surface protein labeling with small-molecule probes" 2007. *Nat. Biotechnol.* 25(12):1483-1487.

Fleischmann et al. "Modification of Polymer Surfaces by Click Chemistry" 2008. *Macromol. Rapid. Commun.* 29:1177-1185.

Fournier et al. "Clicking polymers: a straightforward approach to novel macromolecular architectures" 2007. *Chem. Rev. Soc.* 36:1369-1380.

Gaetke et al. "Copper toxicity, oxidative stress, and antioxidant nutrients" 2003. *Toxicology.* 189:147-163.

Gaucher et al. "Block copolymer micelles: preparation, characterization and application in drug delivery" 2005. *J. Control Release.* 109:169-188.

Gierlich et al. "Click Chemistry as a Reliable Method for the High-Density Postsystematic Functionalization of Alkyne-Modified DNA" 2006. *Org. Lett.* 8(17):3639-3642.

Gramlich et al. "Postsynthetic DNA Modification through the Copper-Catalyzed Azide-Alkyne Cycloaddition Reaction" 2008. *Angew. Chem. Int. Ed.* 47:8350-8358.

Green et al. "Avidin and streptavidin" 1990. *Methods Enzymol.* 184:51-67.

Hanson et al. "Tailored glycoproteomics and glycan site mapping using saccharide-selective bioorthogonal probes" 2007. *J. Am. Chem. Soc.* 129(23):7266-7267.

Hein et al. "Copper-catalyzed azide-alkyne cycloaddition (CuAAC) and beyond: new reactivity of copper(1) acetylides" 2010. *Chem. Soc. Rev.* 39:1302-1315.

Iha et al. "Applications of Orthogonal "Click" Chemistries in the Synthesis of Functional Soft Materials" 2009. *Chem. Rev.* 109:5620-5686.

Im et al. "Patterning Nanodomains with Orthogonal Functionalities: Solventless Synthesis of Self-Sorting Surfaces" 2008. *J Am. Chem. Soc.* 130:14424-14425.

Inouye et al. "The Configurations of $N$-Methyl- and $N$-$t$-Butyl-$\alpha$-methoxycarbonylmethanimine $N$-Oxides" 1983. *Bull. Chem. Soc. Jpn.* 56:3541-3542.

Jacobs et al. "Systems Analysis of Protein Modificatin and Cellular Responses Induced by Electrophile Stress" 2010. *Acc. Chem. Res.* 43(5):673-683.

Jewett et al. "Rapid Cu-Free Click Chemistry with Readily Synthesized Biarylazacyclooctynones" 2010. *J. Am. Chem. Soc.* 132:3688-3690.

Johnson et al. "Copper-free click chemistry for the in situ crosslinking of photodegradable star polymers" 2008. *Chem. Commun.* 3064-3066.

Jung et al. "Direct Synthesis of Dibenzocyclooctadienes via Double Ortho Friedel-Crafts Alkylation by the Use of Aldehyde-Trimethylsilyl Iodide Adducts" 1978. *J. Org. Chem.* 43(19):3698-3701.

Jung et al. "Total Synthesis of Isopavine and Intermediates for the Preparation of Substituted Amitriptyline Analogues: Facile Routes to Substituted Dibenzocyclooctatrienes and Dibenzocycloheptatrienes" 1981. *J. Am. Chem.* 103(8):1984-1992.

Kalesh et al. "The use of click chemistry in the emerging field of catalomics". 2010. *Org. Biomol. Chem.* pp. 1-14.

Kho et al. "A tagging-via-substrate technology for detection and proteomics of farnesylated proteins" 2004. *Proc. Natl. Acad. Sci. USA* 101(34):12479-12484.

Kolb et al. "The growing impact of click chemistry on drug discovery" 2003. *Drug Discovery Today.* 8(24):1128-1137.

Ku et al. "Surface Patterning with Fluorescent Molecules Using Click Chemistry Directed by Scanning Electrochemical Microscopy" *J. Am. Chem. Soc.* 2008. 130:2392-2393.

Kuzmin et al. "Surface Funcitonalization Using Catalyst-Free Azide-Alkyne Cycloaddition" 2010. *Bioconjugate Chem.* 21(11):2076-2085.

Landi et al. "Synthesis and Application of a New Cleavable linker for "click"-based affinity chromatography" 2010. *Org. Biomol. Chem.* 8:56-59.

Lau et al. "Capture and Analysis of Quantitative Proteomic Data" 2007. *Proteomics.* 7(16):2787-2799.

Laughlin et al. "In Vivo Imaging of Membrane-Associated Glycans in Developing Zebrafish" 2008. *Science.* 320:664-667.

Lavasanifar et al. "Poly(ethylene oxide)-*block*-poly (L-amino acid) micelles for drug delivery" 2002. *Adv. Drug Delivery Rev.* 54:169-190.

Laverman et al. "In-Depth evaluation of the cycloaddition-retro-Diels-Alder reaction for in vivo targeting with [$^{111}$In]-DTPA-RGD conjugates" 2009. *Nuclear Medicine and Biology.* 36:749-757.

Lee et al. "An efficient and practical method for the synthesis of mono-$N$-protected $\alpha,\omega$-diaminoalkanes" 2001. *Tetrahedron Lett.* 42:2709-2711.

Lim et al. "Bioorthogonal Chemistry: Recent Progress and Future Directions" 2010. NIH Public Access. Retrieved from the Internet on Jul. 1, 2013. Retrieved from the Internet URL: http://www.ncbi.nlm.nih.gov/pmc/articles/UMC2914230/?report=reader . 17 pages.

Link et al. "Cell Surface Labeling of *Escherichia coli* via Copper (I)-Catalyzed [3+2] Cycloaddition" 2003. *J. Am. Chem. Soc.* 125:11164-11165.

Link et al. "Discovery of aminoacyl-tRNA synthetase activity through cell-surface display of noncanonical amino acids" 2006. *Proc. Natl. Acad. Sci. U.S.A.* 103(27):10180-10185.

Luchansky et al. "Azido Sialic Acids Can Modulate Cell-Surface Interactions" 2004. *Chem.-BioChem.* 5:1706-1709.

Mader et al. "Surface-Modified Upconverting Microparticles and Nanoparticles for Use in Click Chemistries" 2010. *Chem. Eur. J.* 16:5416-5424.

Mamidyala et al. "In situ click chemistry: probing the binding landscapes of biological molecules" 2010. *Chem. Soc. Rev.* 39:1252-1261.

Michel et al. Carbohydrate Microarrays by Microcontact "Click" Chemistry 2008. *Langmuir.* 24:12116-12118.

Moses et al. "The growing applications of click chemistry" 2007. *Chem. Soc. Rev.* 36:1249-1262.

Nandivada et al. "Click Chemistry: Versatility and Control in the Hands of Materials Scientists" 2007. *Adv. Master.* 19:2197-2208.

Nebhani et al. "Orthogonal Transformations on Solid Substrates: Efficient Avenues to Surface Modification" 2009. *Adv. Mat.* 21:3442-3468.

Nessen et al. "Selective Enrichment of Azide-Containing Peptides from Complex Mistures" 2009. *J. Proteome Res.* 8:3702-3711.

Ning et al. "Visualizing Metabolically Labeled Glycoconjugates of Living Cells by Copper-Free and Fast Huisgen Cycloadditionsl3" 2008. *Angew. Chem. Int. Ed.* 47:2253-2255.

Nishiyama et al. "Nanostructured Devices Based on Block Copolymer Assemblies for Drug Delivery: Designing Structures for Enhanced Drug Function" 2006. *Adv. Polym. Sci.* 193:67-101.

Ochiai et al. "Expeditious Chemoenzymatic Synthesis of Homogeneous N-Glycoproteins Carrying Defined Oligosaccharide Ligands" 2008. *J. Am. Chem. Soc.* 130:13790-13803.

Poloukhtine et al. "Selective Labeling of Living Cells by a Photo-Triggered click Reaction" 2009. *J. Am. Chem. Soc.* 131:15769-15776.

Prescher et al. "Chemistry in living systems" 2005. *Nat. Chem. Biol.* 1(1):13-21.

Ratner et al. "Biomaterials Science: an introduction to materials in medicine" 2004. *Academic Press.* San Diego, CA. Title Page, Copyright Page, Table of Contents. 6 pages.

Rosler et al. "Advanced drug delivery devices via self-assembly of amphiphilic block copolymers" 2001. *Adv. Drug Delivery Rev.* 53:95-108.

Rostovtsev et al. "A Stepwise Huisgen Cycloaddition Process: Copper(I)-Catalyzed Regioselective "Ligation" of Azides and Terminal Alkynes" 2002. *Angew. Chem.* 114(Nr. 14):2708-2711.

(56) References Cited

OTHER PUBLICATIONS

Rostovtsev et al. "A Stepwise Huisgen Cycloaddition Process: Copper(1)-Catalyzed Regioselective "Ligation" of Azides and Terminal Alkynes" 2002. *Angew. Chem. Int. Ed.* 41(14):2596-2599.

Schwabacher et al. "Desymmetrization Reactions: Efficient Preparation of Unsymmetrically Substituted Linker Molecules" 1998. *J. Org. Chem.* 63:1727-1729.

Seitz et al. "5,6-Didehydro-11,12-dihydrodibenzo($\alpha$,e)cycloocten" 1969. *Angew. Chem.* 81:427-428.

Seitz et al. "5,6-Didehydro-11, 12-dihydrodibenzo($\alpha$,e)-cyclooctene" 1969. *Angew. Chem. Int. Ed.* 8:447-448.

Singh et al. "Efficient Synthesis of DNA Conjugates by Strain-Promoted Azide-Cyclooctyne Cycloaddition in the Solid Phase" 2011. *Eur. J Org. Chem.* 6739-6746.

Sivakumar et al. "A Fluorogenic 1,3-Dipolar Cycloaddition Reaction of 3-Azidocoumarins and Acetylenes" 2004. *Org. Lett.* 6(24):4603-4606.

Sletten et al. "A Hydrophilic Azacyclooctyne for Cu-Free Click Chemistry" 2008. *Org. Lett.* 10(14):3097-3099.

Speers et al. "Activity-Based Protein Profiling in Vivo Using a Copper (1)-Catalyzed Azide-Alkyne [3+2] Cycloaddition" 2003. *J. Am. Chem. Soc.* 125:4686-4687.

Starke et al. "A novel dibenzoazacyclooctyne precursor in regioselective copper-free click chemistry. An innovative 3-step synthesis". 2010. ARKIVOC 2010 (xi) 350-359.

Sun et al. "Carbohydrate and Protein Immobilization onto Solid Surfaces by Sequential Diels-Alder and Azide-Alkyne Cycloadditions" 2006. *Bioconjugate Chem.* 17:52-57.

Too. "Soluble polymer-based isotopic labeling (SoPIL): a new strategy to discover protein biomarkers?" 2007. *Expert Rev. Proteomics.* 4(5):603-607.

Tornoe et al. "Peptidotriazoles on Solid Phase: [1,2,3,]-Triazoles by Regiospecific Copper(I)-Catalyzed 1,3-Dipolar Cycloadditions of Terminal Alkynes to Azides" 2002. *J. Org. Chem.* 67:3057-3064.

Turner et al. "Heats of Hydrogenation. IX. Cyclic Acetylenes and Some Miscellaneous Olefins" 1973. *J. Am. Chem. Soc.* 95(3):790-792.

vanBerkel et al. "Metal-Free Triazole Formation as a Tool for bioconjugation" 2007. *Chem-BioChem.* 8:1504-1508.

Wang et al. "Bioconjugation by Copper(I)-Catalyzed Azide-Alkyne [3+2] Cycloaddition" 2003. *J. Am. Chem. Soc.* 125:3192-3193.

Weisbrod et al. "Novel strategies for the site-specific covalent labeling of nucleic acids" 2008. *Chem. Commun.* 5675-5685.

Wilchek et al. "Introduction to avidin-biotin technology" 1990. *Methods Enzymol.* 184(2):5-13.

Wilson et al. Noncovalent Cell Surface Engineering with Cationic Graft Copolymers: 2010. *J. Am. Chem. Soc.* 132:2945.

Wittig et al. "On the existence of low-membered cycloalkynes" 1961. *Chem. Ber.* 94:3260-3275, with English Language Machine Translation Abstract (1 pg).

Wong et al. "Selective Covalent Protein Immobilization: Strategies and Applications" 2009. *Chem. Rev.* 109:4025-4053.

Wu et al. "Catalytic Azide-Alkyne Cycloaddition: Reactivity and Applications" 2007. *Aldrichimica Acta.* 40(1):7-17.

Zhang et al. "Bioconjugated Janus Particles Prepared by in Situ Click Chemistry" 2009. *Chem. Mater.* 21:4012-4018.

Zou et al. "Cu-free cycloaddition for identifying catalytic active adenylation domains of nonribosomal peptide synthetases by phage display" 2008. *Bioorg. Med. Chem. Lett.* 18:5664-5667.

Debets et al. "Aza-dibenzoeyetooctynes for fast and efficient enzyme PEGylation via copper-free (3+2) dipolar cycloaddition". Supplementary Material for *Chem. Commun.* 46:97-99 (2009). 13 pages.

* cited by examiner

AZA-DIBENZOCYCLOOCTYNES AND METHODS OF MAKING AND USING SAME

This application claims the benefit of U.S. Provisional Application No. 61/368,775, filed Jul. 29, 2010, which is herein incorporated by reference in its entirety.

BACKGROUND

Surface immobilization of biomolecules is a very important step in the manufacturing of biosensors, microbeads, biochips, probe arrays, medical implants, and other devices. The key requirements for this process are the preservation of biochemical properties of immobilized substrates and robustness of the linkage. Copper (I)-catalyzed Huisgen 1,3-dipolar cycloaddition of azides to terminal acetylenes has emerged as one of the most convenient methods for the functionalization of various surfaces. The triazol linker fowled in the azide "click" reaction has excellent chemical stability due to the aromatic character of the formed heterocycle. Azide tags can be incorporated into biomolecules using a variety of different strategies, such as post-synthetic modification, in vitro enzymatic transfer, the use of covalent inhibitors, and metabolic labeling by feeding cells a biosynthetic precursor modified with azido functionality. While conventional copper (I)-catalyzed click chemistry has become commonplace in surface derivatization, as well as polymer and materials synthesis, the use of metal catalyst often limits the utility of the method. Copper ions are cytotoxic, can cause degradation of DNA molecules, and induce protein denaturation. In addition, the use of catalysts complicates kinetics of the immobilization process, requires polar solvents, and can alter surface properties.

Conventional azide click coupling methods employ terminal acetylenes, since internal alkynes react with azides only at elevated temperatures. Cyclooctynes, on the other hand, are known to form triazoles without a catalyst under ambient conditions, albeit at rather slow rate. The triple bond incorporated into an eight-membered ring is apparently already bent into a geometry resembling the transition state of the cycloaddition reaction, thus reducing its activation barrier. Recently-developed cyclooctyne derivatives are substantially more reactive towards azides and offer a convenient metal-free alternative to the copper-catalyzed click reaction (e.g., Jewett et al., *J. Am. Chem. Soc.* 2010, 132:3688-3690; Ning et al., *Angew. Chem., Int. Ed.* 2008, 47:2253-2255; and Debets et al., *Chem. Commun.* 2010, 46:97-99). Metal-free click chemistry has been successfully employed for the modification of luminescent quantum dots, proteins labeling and purification, as well as for the introduction of fluorescent tags into live cells (Poloukhtine et al., *J. Am. Chem. Soc.* 2009, 131: 15769-15776) and organisms.

There remains a continuing need for new materials and methods for coupling azides to alkynes.

SUMMARY

In one aspect, the present disclosure provides an alkyne of the formula:

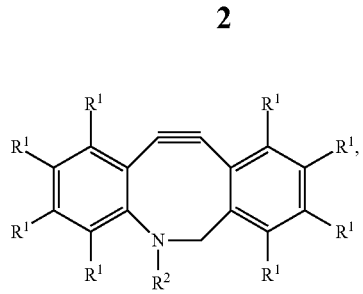

Formula II wherein: each $R^1$ independently represents H or an organic group; $R^2$ represents a —C(O)—$R^4$ group; and $R^4$ represents an organic group attached to a surface (e.g., by hydrogen bonding and/or covalent bonding). In some embodiments each $R^1$ is hydrogen. The surface can be a surface of a wide variety of materials including, but not limited to, biological materials, particles, polymers, glasses, oxides, or combinations thereof.

In another aspect, the present disclosure provides a method of preparing a heterocyclic compound.

In one embodiment, the method includes: combining at least one azide of the formula $R^3$—$N_3$ with at least one alkyne of the formula:

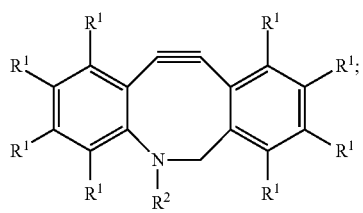

Formula II and allowing the at least one azide and the at least one alkyne to react under conditions effective to form a heterocyclic compound of one or more of the following formulas:

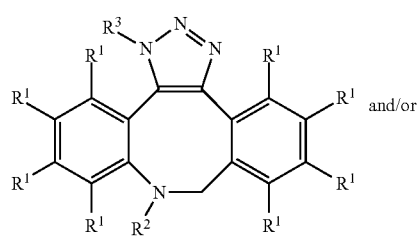

Formula III and/or

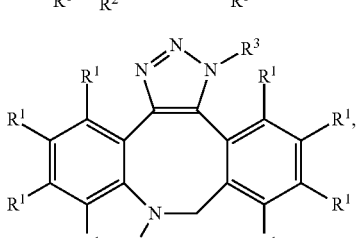

Formula IV wherein: each $R^1$ independently represents H or an organic group; $R^2$ represents a —C(O)—$R^4$ group; $R^3$ represents an organic group; and $R^4$ represents an organic group attached to a surface. In certain embodiments, conditions effective to form the heterocyclic compound include the substantial absence of added catalyst. In certain embodiments, $R^3$ can include a detectable label (e.g., an affinity label), and the method includes labeling the surface. Optionally, the method further includes detecting the heterocyclic compound.

In another embodiment, the method includes: combining at least one azide of the formula R³—N₃ with at least one alkyne of the formula:

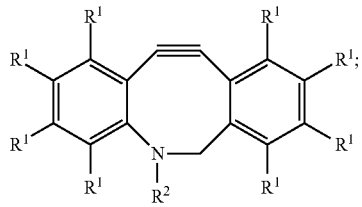

Formula II and allowing the at least one azide and the at least one alkyne to react under conditions effective to faun a heterocyclic compound of one or more of the following formulas:

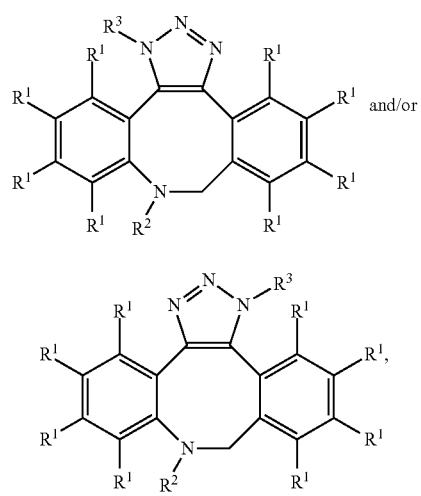

Formula III and/or

Formula IV wherein: each $R^1$ independently represents H or an organic group; $R^2$ represents a —C(O)—$R^4$ group; $R^3$ represents an organic group attached to a surface; and $R^4$ represents an organic group. In certain embodiments, conditions effective to fatal the heterocyclic compound include the substantial absence of added catalyst. In certain embodiments, $R^4$ can include a detectable label (e.g., an affinity label), and the method includes labeling the surface. Optionally, the method can further include detecting the heterocyclic compound.

In yet another aspect, the present disclosure provides a method of preparing a heterocyclic alkyne. In one embodiment, the method includes: subjecting a compound of the formula:

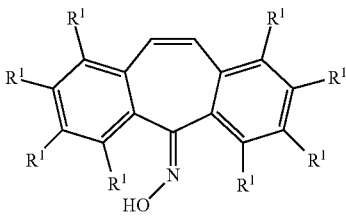

Formula V to conditions effective for a Beckman rearrangement to provide a lactam of the formula:

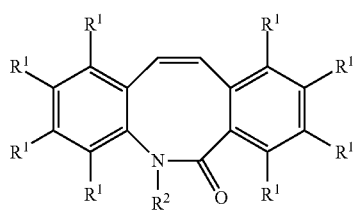

Formula VI wherein each $R^1$ independently represents H or an organic group, and $R^2$ is H; subjecting the lactam of Formula VI to conditions effective to reduce the lactam and provide the heterocyclic alkene of the formula:

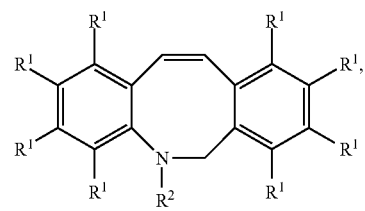

Formula I wherein each $R^1$ independently represents H or an organic group, and $R^2$ is H; converting $R^2$ from H to a —C(O)—$R^4$ group, wherein $R^4$ represents an organic group; and subjecting the converted heterocyclic alkene to conditions effective to convert the alkene to an alkyne of the formula:

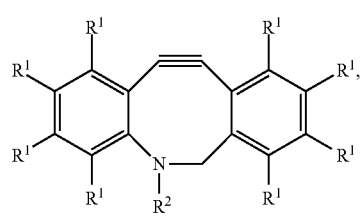

Formula II wherein each $R^1$ independently represents H or an organic group; $R^2$ represents a —C(O)—$R^4$ group; and $R^4$ represents an organic group.

The high reactivity of the ADIBO alkynes disclosed herein can be advantageous for reactions with azides for a wide variety of applications including, for example, labeling and/or derivatizing surfaces. Further, convenient methods of preparing such ADIBO alkynes are disclosed herein.

DEFINITIONS

The term "comprises" and variations thereof do not have a limiting meaning where these terms appear in the description and claims.

As used herein, "a," "an," "the," "at least one," and "one or more" are used interchangeably.

As used herein, the term "or" is generally employed in the sense as including "and/or" unless the context of the usage clearly indicates otherwise.

Also herein, the recitations of numerical ranges by endpoints include all numbers subsumed within that range (e.g., 1 to 5 includes 1, 1.5, 2, 2.75, 3, 3.80, 4, 5, etc.).

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
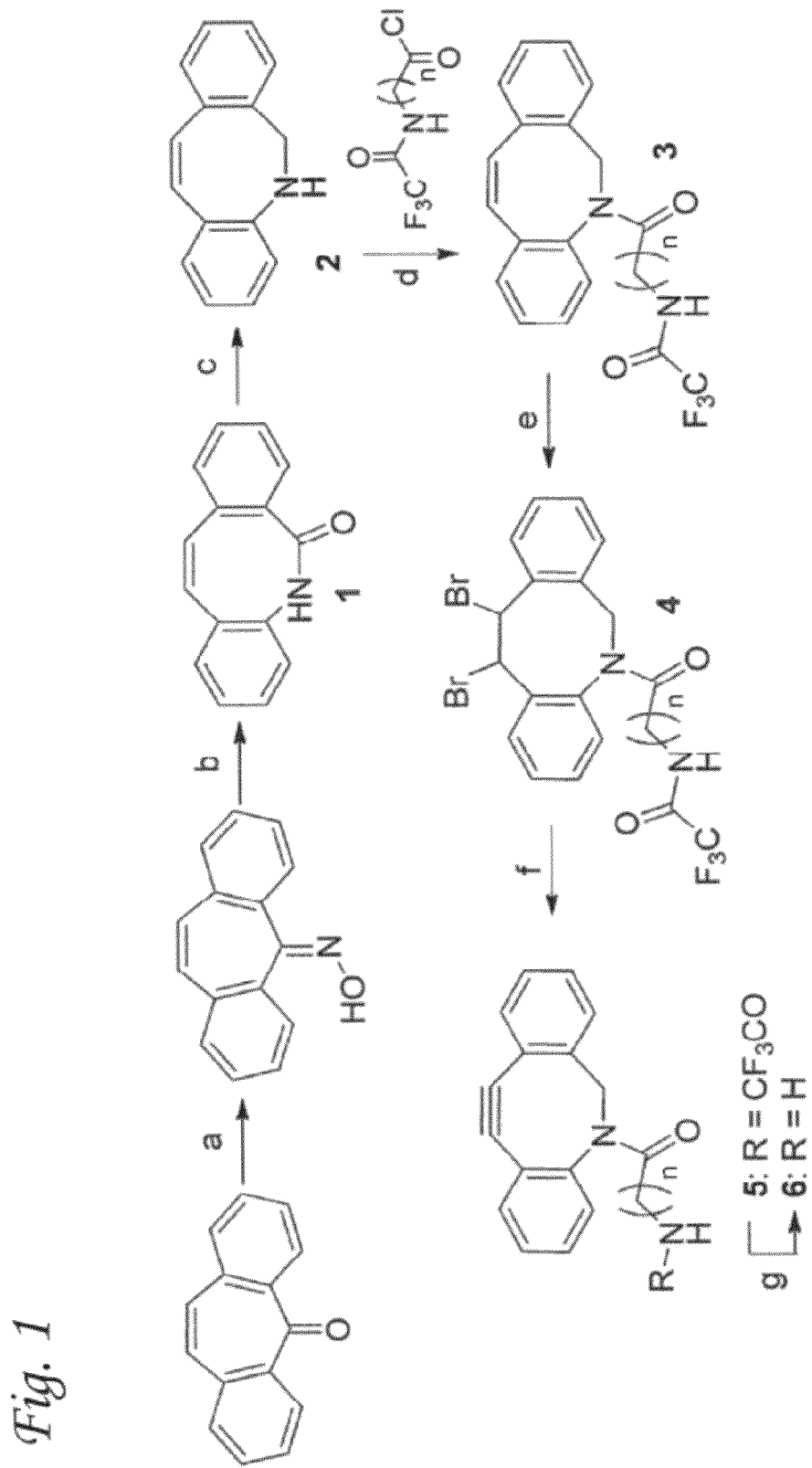
FIG. 1 is a schematic illustration showing an embodiment of a method for preparing an exemplary aza-dibenzocyclooctyne-amine (ADIBO-amine 6) (e.g., ADIBO-C6-amine for n=5). Reagents and conditions: (a) NH$_2$OH.HCl, pyridine, 60%; (b) PPA, 125° C., 73%; (c) LiAlH$_4$, ether, 58%; (d) pyridine, CH$_2$Cl$_2$, 71%; (e) pyridinium tribromide, 78%; (f) t-BuOK, THF, 88%; (g) K$_2$CO$_3$, aq MeOH, 58%.

Substitution of one of the saturated carbons in the cyclooctyne ring for a nitrogen atom not only improves its reactivity, but also simplifies the synthesis (Jewett et al., *J. Am. Chem. Soc.* 2010, 132:3688-3690; and Debets et al., *Chem. Commun.* 2010, 46:97-99). To extend arsenal of bioorthogonal copper-free click reagents, an efficient synthesis of aza-dibenzocyclooctyne (ADIBO)-containing compounds for azide-coupling reactions has been developed. In the present disclosure, a novel approach for efficient surface-functionalization using a catalyst-free azide click reaction is disclosed herein. This method allows for the site-specific covalent anchoring of proteins and other substrates to various surfaces. The same metal-free click reaction is employed for the PEGylation of unfunctionalized areas of the surface. Such treatment allows for a dramatic reduction or complete elimination of non-specific binding. The copper-free click immobilization strategy discussed in the present report can be applied to the preparation of various types of arrays, as well as to the derivatization of microbeads and nanoparticles.

The utility of catalyst-free azide-alkyne [3+2] cycloaddition for the immobilization of a variety of molecules onto a solid surface and microbeads was demonstrated. In this process, the surfaces were derivatized with aza-dibenzocyclooctyne (ADIBO) for the immobilization of azide-tagged substrates via a copper-free click reaction. Alternatively, ADIBO-conjugated molecules can be anchored to the azide-derivatized surface. Both immobilization techniques work well in aqueous solutions and show excellent kinetics under ambient conditions. An efficient synthesis of aza-dibenzocyclooctyne (ADIBO) has been developed, which is among the most reactive cyclooctynes for cycloaddition to azides, in addition to being a convenient cyclooctyne to prepare and being a cyclooctyne having excellent stability. Convenient methods for the conjugation of ADIBO with a variety of molecules directly or via a PEG linker is also disclosed herein.

In one aspect, the present disclosure provides a method of preparing a heterocyclic alkene. In one embodiment, the method includes: subjecting a compound of the formula:

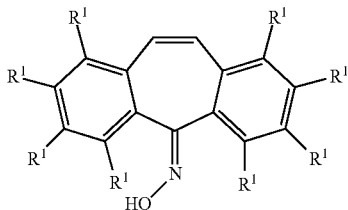
Formula V to conditions effective for a Beckman rearrangement to provide a lactam of the formula:

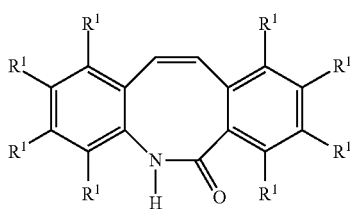
Formula VI wherein each $R^1$ independently represents H or an organic group, and $R^2$ is H; and subjecting the lactam of Formula VI to conditions effective to reduce the lactam and provide a heterocyclic alkene of the formula:

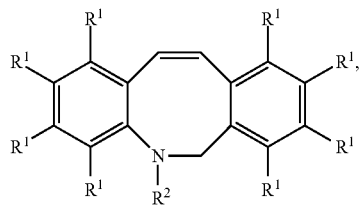
Formula I wherein: each $R^1$ independently represents H or an organic group (e.g. a C1-C12 organic group, and in some embodiments a C1-C12 hydrocarbon moiety); and $R^2$ is H. In some embodiments each $R^1$ represents H. Exemplary conditions for the Beckman rearrangement can include, for example, treatment with polyphosphoric acid at a temperature of 25° C. to 200° C. Exemplary conditions to reduce the lactam can include, for example, treatment with lithium aluminum hydride under anhydrous conditions, optionally in the presence of an aprotic solvent.

In some embodiments, the method can further include converting $R^2$ from H to a $—C(O)—R^4$ group, wherein $R^4$ represents an organic group. Optionally, the converted heterocyclic alkene can be subjected to conditions effective to convert the alkene to an alkyne of the formula:

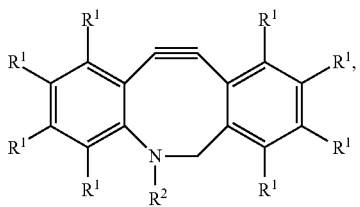
Formula II wherein: each $R^1$ independently represents H or an organic group, $R^2$ represents a $—C(O)—R^4$ group, and $R^4$ represents an organic group. $R^4$ can represent a wide variety of organic groups that can include, for example, detectable labels (e.g., dyes) and/or linking groups for attaching the alkyne to a surface. In some embodiments, conditions effective to convert the alkene to the alkyne can include: halogenating the alkene to form a dihalide; and dehydrohalogenating the dihalide to form the alkyne. For example, the alkene can be brominated to form the dibromide, followed by dehydrobrominating to form the alkyne.

For example, an efficient preparation of an ADIBO-amine, aza-dibenzocyclooctyne-amine conjugate (ADIBO-amine 6), is outlined in FIG. 1. Dibenzosuberenone oxime can be readily prepared by treating commercially-available dibenzosuberenone with hydroxylamine. The dibenzosuberenone oxime can then be treated with polyphosphoric acid to catalyze a Beckman rearrangement of the dibenzosuberenone oxime to lactam 1. Lactam 1 can then be reduced, for example, with lithium aluminum hydride, to give dihydrodibenzo[b,f]azocine (2). The secondary amino group in 2 can be converted to amide 3, for example, by reacting with 1.25 eq. of an w-(trifluoroacetamido)alkanoyl chloride with n=1 to 18 (e.g., 6-(trifluoroacetamido)hexanoyl chloride for n=5) in the presence of pyridine. The olefin in 3 can be readily converted into an acetylene moiety via a bromination-dehydrobromination procedure to give aza-dibenzocyclooctyne 5 in high yield (88%). Saponification of the trifluoroacetamide moiety with potassium carbonate in aqueous methanol gives an ADIBO-amine (6) (e.g., ADIBO-C6-amine for n=5). An ADIBO-amine with a shorter aminoakyl side chain, ADIBO-C3-amine (7) for n=3, was also prepared following the same synthetic sequence by replacing 6-(trifluoroacetamido)hexanoyl chloride in step "d" with 3-(trifluoroacetamido)propionyl chloride.

Figure 2:
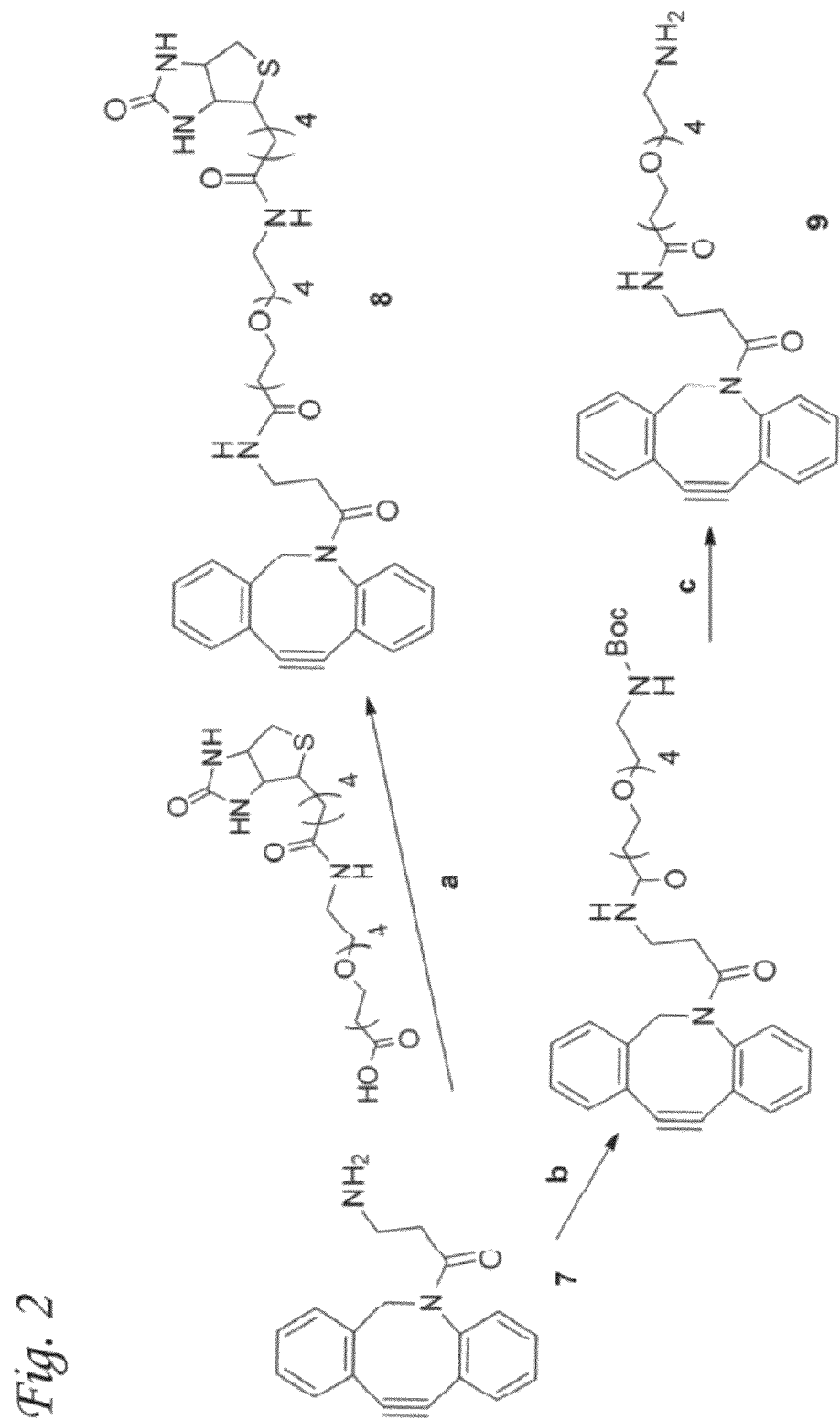
FIG. 2 is a schematic illustration showing an embodiment of a method for preparing exemplary aza-dibenzocyclooctynes, ADIBO-biotin (8) and ADIBO-PEG$_4$-amine (9). Reagents and conditions: (a) HBTU, DIEA, CH$_2$Cl$_2$, 89%; (b) Boc-NH—(CH$_2$CH$_2$O)$_4$—CH$_2$CH$_2$CO$_2$H, EDC, DIEA, CH$_2$Cl$_2$, 80%; (c) TFA, THF, 79%.

The ADIBO-amines can then be used to prepare additional materials. For example, aza-dibenzocyclooctyne-biotin conjugate (ADIBO-biotin, 8) was prepared by HBTU (1-[bis(dimethylamino)methylene]-1H-benzotriazolium-3-oxide hexafluorophosphate)-promoted coupling of ADIBO-C3-amine (7) with biotin-PEG$_4$-acid (FIG. 2). EDC-induced coupling of compound 7 with N-Boc-15-amino-4,7,10,13-tetraoxapentadecanoic acid, followed by trifluoroacetic acid-catalyzed removal of N-Boc protection gave aza-dibenzocyclooctyne-PEG$_4$-amine (ADIBO-PEG$_4$-amine, 9, FIG. 2). Additional ADIBO-amines are disclosed in the working examples.

In another aspect, the present disclosure provides an alkyne of the formula:

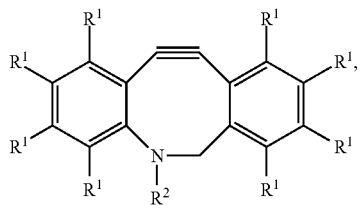

Formula II wherein: each R$^1$ independently represents H or an organic group (e.g. a C1-C12 organic group, and in some embodiments a C1-C12 hydrocarbon moiety); R$^2$ represents a —C(O)—R$^4$ group; and R$^4$ represents an organic group attached to a surface (e.g., by hydrogen bonding and/or covalent bonding). In some embodiments each R$^1$ is hydrogen. The surface can be a surface of a wide variety of materials including, but not limited to, biological materials, particles, polymers, glasses, oxides, or combinations thereof.

In another aspect, the present disclosure provides a method of preparing a heterocyclic compound.

In one embodiment, the method includes: combining at least one azide of the formula R$^3$—N$_3$ with at least one alkyne of the formula:

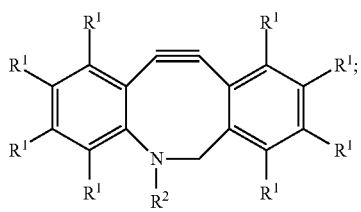

Formula II and allowing the at least one azide and the at least one alkyne to react under conditions effective to form a heterocyclic compound of one or more of the following formulas:

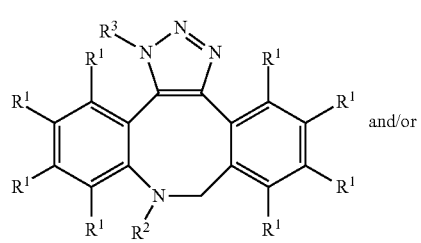

Formula III and/or

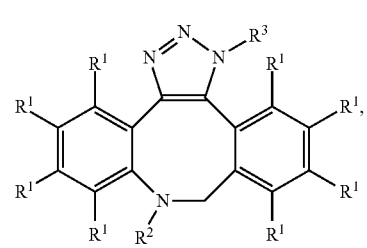

Formula IV wherein: each R$^1$ independently represents H or an organic group (e.g. a C1-C12 organic group, and in some embodiments a C1-C12 hydrocarbon moiety); R$^2$ represents a —C(O)—R$^4$ group; R$^3$ represents an organic group; and R$^4$ represents an organic group attached to a surface. In certain embodiments, conditions effective to form the heterocyclic compound include the substantial absence of added catalyst. In certain embodiments, R$^3$ can include a detectable label (e.g., an affinity label), and the method includes labeling the surface. Optionally, the method further includes detecting the heterocyclic compound.

In another embodiment, the method includes: combining at least one azide of the formula R$^3$—N$_3$ with at least one alkyne of the formula:

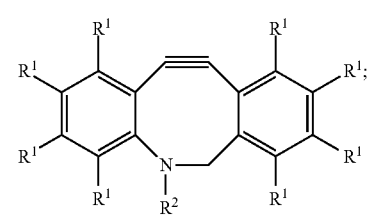

Formula II and allowing the at least one azide and the at least one alkyne to react under conditions effective to form a heterocyclic compound of one or more of the following formulas:

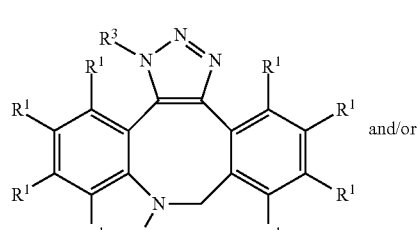

Formula III and/or

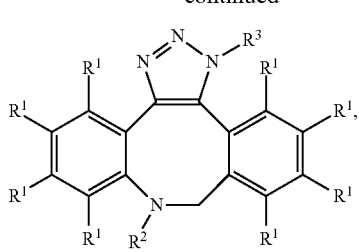

Formula IV wherein: each $R^1$ independently represents H or an organic group (e.g. a C1-C12 organic group, and in some embodiments a C1-C12 hydrocarbon moiety); $R^2$ represents a —C(O)—$R^4$ group; $R^3$ represents an organic group attached to a surface; and $R^4$ represents an organic group (e.g. a C1-C12 organic group, and in some embodiments a C1-C12 hydrocarbon moiety). In certain embodiments, conditions effective to form the heterocyclic compound include the substantial absence of added catalyst. In certain embodiments, $R^4$ can include a detectable label (e.g., an affinity label), and the method includes labeling the surface. Optionally, the method can further include detecting the heterocyclic compound.

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for compounds of this invention are those that do not interfere with the reaction of an alkyne with a 1,3-dipole-functional compound to form a heterocyclic compound. In the context of the present invention, the term "aliphatic group" means a saturated or unsaturated linear or branched hydrocarbon group. This term is used to encompass alkyl, alkenyl, and alkynyl groups, for example. The term "alkyl group" means a saturated linear or branched monovalent hydrocarbon group including, for example, methyl, ethyl, n-propyl, isopropyl, tert-butyl, amyl, heptyl, and the like. The term "alkenyl group" means an unsaturated, linear or branched monovalent hydrocarbon group with one or more olefinically unsaturated groups (i.e., carbon-carbon double bonds), such as a vinyl group. The term "alkynyl group" means an unsaturated, linear or branched monovalent hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

Additional methods of making and using aza-dibenxocyclooctynes are disclosed in the examples. The present invention is illustrated by the following examples. It is to be understood that the particular examples, materials, amounts, and procedures are to be interpreted broadly in accordance with the scope and spirit of the invention as set forth herein.

EXAMPLES

Example 1

Materials and Methods

Purification of products by column chromatography was performed using 40-63 μm silica gel. All NMR spectra were recorded on 400 MHz instrument in $CDCl_3$ and referenced to TMS unless otherwise noted. Images of fluorophore-patterned slides were recorded and fluorescence intensity was quantified using Typhoon 9400 Variable Mode Imager (GE Healthcare) at an excitation/emission setting appropriate for fluorescein (488/520 nm) or a fluorophore available under the trade designation Lissamine rhodamine B (532/580 nm) fluorophores in PBS solution; images of fluorescent microbeads were obtained using Zeiss Observer AX10 inverted microscope with a X-cite Series 120 fluorescent light source and Chroma Technology filters. The relative fluorescent intensity (spot/background) was quantified using ImageJ (NIH) program.

Tetrahydrofuran was distilled from a sodium/benzophenone ketyl; ether and hexanes were distilled from sodium; N,N-Dimethylfoiniamide (DMF) was dried by passing through an alumina column. An azide available under the trade designation Biotin-dPEG 3+4-azide and Biotin-$PEG_4$-acid were purchased from Quanta BioDesign; fluorescein SE, a dye available under the trade designation Oregon Green SE, Lissamine rhodaraine B sulfonyl chloride, and FITC-Avidin were obtained from Invitrogen; (3-glycidyloxypropyl) dimethoxymethylsilane was purchased from TCI America; 0.0067 M phosphate buffered saline (PBS) with pH 7.4 was obtained from Thermo Scientific. Bovine Serum Albumin (BSA) was obtained under the trade designation Fisher BioReagents from Fisher Scientific. Other reagents were purchased from Aldrich or VWR and used as received unless otherwise noted. Polished glass slides were obtained from VWR; streptavidin magnetic microspheres available under the trade designation NanoLink microspheres (1% aqueous suspension) were purchased from SoluLink Biosciences. Aza-dibenzocycloctyne 6 conjugates with fluorescein (ADIBO-fluor, 10), Oregon Green (ADIBO-OG, 11), and Lissamine rhodamine B (ADIBO-Rhodamine, 12) were prepared by treating 6 with equimolar amounts of fluorescein SE, Oregon Green SE, Lissamine rhodamine B sulfonyl chloride respectively in DMF in the presence of DIEA (ethyldiisopropylamine). Oregon Green azide (13) and Lissamine rhodamine B azide (14) were prepared by reacting equimolar amounts of Oregon Green SE or Lissamine rhodamine B sulfonyl chloride with 3-azidopropyl amine in DMF in the presence of DIEA. Conjugates 10-14 were purified by chromatography (CHCl$_3$:MeOH:AcOH 100:5:0.5) and their purity was confirmed by HPLC analysis. 1-Amino-11-azido-3,6,9-trioxaundecane (AminoPEG$_4$azide) (Schwabacher et al., *J. Org. Chem.* 1998, 63:1727-1729) and 6-azidohexylamine (Lee et al., *Tetrahedron Lett.* 2001, 42:2709-2711) were prepared according to literature procedures.

5,6-Dihydrodibenzo[b,f]azocine (2)

A solution of dibenzosuberenone (25 g, 121 mmol) and hydroxylamine hydrochloride (6.81 mL, 164 mmol) in pyridine (70 mL) was refluxed for 20 hours. The reaction mixture was concentrated and poured into 5% aqueous hydrochloric acid (with crushed ice), stirred for 20 minutes, filtered, and dried in the air to provide 28.1 g of crude dibenzosuberenone oxime, as a white precipitate. Dibenzosuberenone oxime (16 g, 72.3 mmol) was added to 250 mL polyphosphoric acid at 125° C., the reaction mixture was stirred for 60 minutes at this temperature, poured onto crushed ice (approximately 700 mL), stirred for another 30 minutes, and filtered. The filter cake was washed with water, and dried under vacuum to provide crude dibenzo[b,f]azocin-6(5H)-one 1 (11.6 g, 52.4 mmol, 73%) as a grey powder.

A suspension of 1 (7.4 g, 33.4 mmol) and lithium aluminum hydride (2.494 ml, 66.9 mmol) in anhydrous ether (200 mL) was refluxed for 15 hours. The reaction mixture was quenched by water, filtered, and the filter cake was washed with ether. The filter cake was dispersed in ether (100 mL), stirred for 10 minutes, and filtered. The combined organic layers were dried over MgSO$_4$, solvent was removed under vacuum, and the product purified by chromatography to provide 4.04 g (19.49 mmol, 58%) of 5,6-dihydrodibenzo[b,f]azocine (2). $^1$H, 7.27-7.23 (m, 1H), 7.2-7.1 (m, 3H), 6.96-6.9 (m, 1H), 6.9-6.8 (m, 1H), 6.65-6.55 (m, 1H), 6.54-6.48 (m, 1H), 6.40 (d, J=8 Hz, 1H), 6.38-6.29 (m, 1H), 4.51 (d, J=6.8 Hz, 2H), 4.2 (br s, 1H); $^{13}$C: 147.3, 139.3, 138.3, 134.9, 132.7, 130.3, 129.0, 128.1, 127.8, 127.6, 127.5, 121.8, 118.1, 117.9, 49.6. HRMS (ESI+) calcd for C$_{15}$H$_{14}$N [M+H]$^+$ 208.1126. found 208.1120.

N-(6-(dibenzo[b,f]azocin-5(6H)-yl)-6-oxohexyl)trifluoroacetamide (3)

6-(trifluoroacetamido)hexanoyl chloride (Clark et al., *Chem. Soc. Perkin Trans.* 1 2001:3312-3324) (0.984 g, 4.52 mmol) was added to a solution of 2 (0.75 g, 3.62 mmol) and pyridine (0.859 g, 10.86 mmol) in CH$_2$Cl$_2$ (approximately 10 ml) at room temperature, and stirred for 30 minutes. The reaction mixture was diluted with CH$_2$Cl$_2$ (approximately 20 mL), washed with water (2×30 mL), dried over anhydrous MgSO$_4$ and the solvent was removed under reduced pressure. The residue was purified by chromatography (hexanes:ethyl acetate 2:3) to provide 1.064 g (2.56 mmol, 71%) of 3 as yellowish oil. $^1$H: δ 7.32-7.22 (m, 4H), 7.19-7.11 (m, 4H), 6.77 (d, J=13.2 Hz, 1H), 6.58 (d, J=13.2 Hz, 1H), 5.46 (d, J=14.8 Hz, 1H), 4.20 (d, J=14.8 Hz, 1H), 3.29-3.15 (m, 2H), 2.09-2.02 (m, 1H), 1.93-1.85 (m, 1H), 1.51-1.32 (m, 4H), 1.25-1.04 (m, 2H); $^{13}$C: 172.7, 157.5, 141.1, 136.1, 135.8, 134.8, 132.4, 131.8, 130.5, 128.5, 128.2, 128.1, 128.0, 127.3, 127.2, 117.5, 114.6, 54.8, 39.6, 34.3, 28.2, 25.9, 24.3; FIRMS (ESI+) m/z calcd for C$_{23}$H$_{24}$F$_3$N$_2$O$_2$ [M+H]$^+$ 417.1790. found 417.1783.

N-(6-Trifluoroacetamidohexanoyl)-5,6-dihydro-11,12-didehydrodibenzo[b,f]azocine (5)

Pyridine hydrobromide perbromide (0.948 g, 2.97 mmol) was added to a solution of 3 (1.05 g, 2.70 mmol) in CH$_2$Cl$_2$ (4 ml) at room temperature, and the reaction mixture was stirred overnight. The reaction mixture was diluted with CH$_2$Cl$_2$ (20 mL), washed with 5% aqueous hydrochloric acid (20 mL), dried over MgSO$_4$, and solvent removed under vacuum. The residue was passed through a short pad of silica gel (CH$_2$Cl$_2$) to give 1.2 g of crude N-(trifluoroacetamidohexanoyl)-5,6,11,12-tetrahydro-11,12-dibromodibenzo[b,f]azocine (4) as an oil. Solution of crude 4 (1.2 g, 2.082 mmol) in THF (5 mL) was added to a solution of potassium t-butoxide (0.584 g, 5.21 mmol) in THF (10 ml) at room temperature, the reaction mixture was stirred for 1 hour, diluted with ethyl acetate (20 mL), washed with 5% aqueous hydrochloric acid, brine, dried over MgSO$_4$, and the solvent was removed under reduced pressure. The crude product was purified by chromatography (hexanes:ethyl acetate, 2:1 to 1:1) to afford 0.76 g (1.834 mmol, 88%) of 5 as brown oil. $^1$H NMR: δ 7.68 (d, J=7.6 Hz, 1H), 7.45-7.21 (m, 7H), 6.79 (br s, 1H), 5.16 (d, J=14.4 Hz, 1H), 3.67 (d, J=13.6 Hz, 1H), 3.22-3.14 (m, 1H), 3.11-3.02 (m, 1H), 2.24-2.16 (m, 1H), 1.41-1.22 (m, 4H), 1.11-0.9 (m, 2H); MS: m/z 414 [M$^+$]. Calcd for C$_{23}$H$_{21}$F$_3$N$_2$O$_2$ 414.

N-(6-Aminohexanoyl)-5,6-dihydro-11,12-didehydrodibenzo[b,f]azocine (ADIBO-C6-amine, 6)

Solution of K$_2$CO$_3$ (2 g, 14.47 mmol) in 15 mL of water was added to a solution of N-(6-Trifluoroacetamido hexanoyl)-5,6-dihydro-11,12-didehydrodibenzo[b,f]azocine (5, 2.95 g, 7.12 mmol) in MeOH (30 mL) at room temperature and stirred overnight. Solvents were removed under reduced pressure, the residue was redissolved in CH$_2$Cl$_2$:ethyl acetate (1:4), washed with brine and water. The organic layer was dried over anhydrous Na$_2$SO$_4$, and concentrated in vacuum. The crude product was purified by chromatography (CH$_2$Cl$_2$:MeOH 10:1 to 10:4) to provide 1.31 g (4.11 mmol, 58%) of 6 as slightly yellow oil. $^1$H NMR: δ 7.71 (d, J=7.6 Hz, 1H), 7.45-7.21 (m, 7H), 5.18 (d, J=14.4 Hz, 1H), 3.63 (d, J=13.6 Hz, 1H), 3.55 (m, 4H), 2.74 (m, 2H), 2.57 (t, J=6.0 Hz, 2H), 2.19 (m, 1H), 1.95 (m, 1H), 1.41-1.05 (m, 6H), 1.11-0.9 (m, 2H); $^{13}$C: 173.3, 151.8, 147.8, 132.3, 132.1, 128.9, 128.2, 128.0, 127.8, 127.5, 126.5, 122.1, 123.0, 114.8, 107.9, 55.8, 41.4, 34.7, 31.9, 26.0, 24.8; HRMS (ESI+) m/z calcd for C$_{21}$H$_{23}$N$_2$O [M+H]$^+$ 319.1810. found 319.1799.

N-(3-Aminopropionyl)-5,6-dihydro-11,12-didehydrodibenzo[b,f]azocine (ADIBO-C3-amine, 7)

was prepared following the same protocol as for the preparation of 6. $^1$H NMR: (500 MHz): 7.68 (d, J=7.5 Hz, 1H), 7.45-7.33 (m, 5H), 7.29 (t, J=7.5 Hz, 1H), 7.25 (t, J=7 Hz, 1H), 5.15 (d, J=14 Hz, 1H), 3.16 (d, J=14 Hz, 1H), 2.82-2.67 (m, 2H), 2.45-2.35 (m, 1H), 2.01-1.92 (m, 1H), 1.6-1.4 (br s, 2H); $^{13}$C, 172.14, 151.48, 148.01, 132.12, 129.08, 128.29, 128.21, 127.99, 127.63, 127.01, 125.43, 122.85, 122.57, 114.97, 107.66, 55.25, 38.25, 38.15; FIRMS (ESI+) calcd for C$_{18}$H$_{17}$N$_2$O [M+H]$^+$ 277.1341. found 277.1339.

Aza-dibenzocyclooctyne-biotin conjugate (ADIBO-biotin, 8)

HBTU (1.916 g, 5.05 mmol) was added to a solution of biotin-PEG$_4$-acid (1.9 g, 3.74 mmol) and DIEA (0.647 g, 5.61 mmol) in CH$_2$Cl$_2$ (15 mL) at room temperature and stirred for 15 minutes. A solution of 7 (1.238 g, 4.12 mmol) in $CH_2Cl_2$ (2 mL) was added dropwise, the reaction mixture was stirred for 3 hours, and concentrated under reduced pressure. The product was purified by chromatography ($CH_2Cl_2$ to $CH_2Cl_2$:MeOH 20:1 to 100:15) to provide 2.44 g (3.32 mmol, 89%) of 8 as colorless semi-solid. $^1$H NMR (500 MHz, $CDCl_3$): δ 7.66 (d, J=7 Hz, 1H), 7.42-7:3 (m, 7H), 7.28-7.25 (m, 1H), 7.05-6.99 (m, 1H), 6.79-6.75 (m, 1H), 6.61 (br s, 1H), 5.13 (d, J=14 Hz, 1H), 4.5-4.45 (m, 1H), 4.32-4.25 (m, 1H), 3.68 (d, J=14 Hz, 1H), 3.65-3.45 (m, 17H), 3.44-3.36 (m, 2H), 3.32-3.22 (m, 2H), 3.15-3.07 (m, 2H), 2.9-2.82 (m, 1H), 2.75-2.65 (m, 1H), 2.55-2.46 (m, 1H), 2.33 (q, J=6 Hz, 2H), 2.2 (t, J=7.5 Hz, 2H), 2.0-1.92 (m, 1H), 1.75-1.6 (m, 4H), 1.45-1.35 (m, 5H); $^{13}$C, 173.51, 171.99, 171.13, 164.01, 151.1, 148.09, 132.13, 129.14, 128.68, 128.21, 127.83, 127.19, 125.58, 123.07, 122.45, 114.72, 107.86, 70.45, 70.43, 70.39, 70.3, 70.17, 70.03, 69.98, 97.17, 61.83, 60.26, 55.69, 55.52, 53.67, 42.0, 40.52, 39.14, 36.79, 35.89, 35.26, 34.71, 28.29, 28.11, 25.63, 18.59, 17.44, 11.88; HRMS (ESI+) m/z calcd for $C_{39}H_{53}N_5O_8S$ $[M+H]^+$ 750.3537. found 750.3542.

Aza-dibenzocyclooctyne-PEG$_4$-amine
(ADIBO-PEG$_4$-amine, 9)

EDC (0.75 g, 4.68 mmol) was added to a solution of Boc-NH—$(CH_2CH_2O)_4$—$CH_2CH_2CO_2H$ (PCT International Application Publication No. WO 2009/053339 A2; Pessi et al.) (1.57 g, 4.32 mmol) in $CH_2Cl_2$ (15 mL) and DTRA (0.7 g, 5.4 mmol) at room temperature and stirred for 15 minutes. A solution of ADIBO-amine 7 (1 g, 3.6 mmol) in $CH_2Cl_2$ (1 mL) was added to the reaction mixture and stirred for 4 hours, at which time the solvent was removed under reduced pressure and the crude product purified by chromatography (ethyl acetate:hexanes 1:1 to 9:1) to provide 1.8 g (2.8 mmol, 80%) of crude N-Boc-protected ADIBO-PEG$_4$-amine (9-Boc) as yellow oil.

A solution of TFA (0.48 g, 4.2 mmol) in THF (15 mL) was added to a solution of 9-Boc (1.8 g, 2.8 mmol) in THF (30 mL) at room temperature. The reaction mixture was stirred overnight and the solvent was removed under reduced pressure. The residue was purified by chromatography ($CH_2Cl_2$:MeOH 10:1 to 10:4) to provide 1.15 g (2.2 mmol, 79%) of ADIBO-PEG$_4$-amine (9) as slightly yellow oil. $^1$H-NMR (500 MHz): 7.67 (d, J=7.5 Hz, 1H), 7.43-7.34 (m, 5H), 7.31 (t, J=7.5 Hz, 1H), 7.29-7.24 (m, 1H), 6.95-6.88 (m, 1H), 5.13 (d, J=14 Hz, 1H), 4.45-4.2 (br s, 2H), 3.7-3.5 (m, 21H), 3.37-3.2 (m, 3H), 2.68 (t, J=5 Hz, 2H), 2.57-2.42 (m, 1H), 2.4-2.32 (m, 2H), 2.02-1.92 (1H); $^{13}$C-NMR (100 MHz, $CDCl_3$): 172.13, 171.21, 151.20, 148.16, 129.3, 129.2, 128.78, 128.44, 128.31, 127.9, 127.29, 127.25, 125.68, 123.16, 122.55, 114.81, 107.92, 70.46, 70.39, 70.35, 70.32, 70.30, 70.26, 70.1, 55.62, 48.86, 36.69, 35.41, 34.67; FIRMS (ESI+) m/z calcd for $C_{29}H_{38}N_3O_6$ [M+H] 524.2761. found 524.2756.

Cleaning and Activation of Glass Slides Surface

All glass slides were sonicated for 30 minutes in methanol, rinsed with acetone, and dried in an oven at 145° C. for 1 hour Piranha solution (90 mL) was prepared by the addition of $H_2O_2$ (25 mL of 35% v/v) in one portion to 65 mL of conc. $H_2SO_4$ in a 100 mT, Pyrex beaker, which was kept in a water bath. Because Piranha solution reacts violently with organic compounds, appropriate cautions should be taken for handling with extreme care, e.g., by wearing thick plastic gloves, a lab coat, and safety glasses, and handling in a fume hood at all times.

The solution was carefully stirred with a glass rod, followed by inserting glass slides into the solution. After 1 hour, slides were removed from the solution and rinsed with copious amounts of distilled water, then acetone, and dried in an oven for 20 minutes at 145° C. Glass slides prepared in this fashion were submitted to derivatization procedures immediately.

Preparation of Epoxy-Derivatized Glass Slides

Freshly-activated glass slides were immersed in a solution of freshly-distilled (3-glycidyloxypropyl)dimethoxy-methylsilane (1% v/v) and DIEA (1% v/v) in dry toluene (100 mL) at 25° C. for 16 hours. Slides were sonicated two times in methanol for 15 minutes, thoroughly rinsed with acetone, and dried under a stream of nitrogen.

Preparation of Aza-Dibenzocyclooctyne (ADIBO, 6)—Coated Glass Slides

Freshly-prepared epoxy-coated glass slides were placed in a solution of aza-dibenzocyclooctyne amine 6 (75 mg) and DIEA (1 mL) in DMF (100 mL) and incubated overnight at room temperature. Slides were then rinsed with acetone, sonicated for 15 minutes in methanol, rinsed with acetone, and dried under a stream of nitrogen.

Preparation of Azide—Coated Glass Slides

Freshly-prepared epoxy-coated glass slides were immersed in a solution of 6-azidohexylamine (1 mL) and DIEA (1 mL) in DMF (100 mL) overnight at room temperature. The slides were then sonicated for 15 minutes in methanol, rinsed with acetone, and dried under a stream of nitrogen.

Patterned Derivatization of Glass Slides with Aza-Dibenzocyclooctyne 6

1 µL drops of 10 mM PBS solution of dibenzocyclooctyne 6 were spotted using a micropipette on a freshly-prepared epoxy-coated slide followed by incubation in a humidity chamber containing PBS buffer for 12 hours at room temperature. The slide was washed with copious amounts of acetone, then water, and sonicated in DMF for 30 minutes.

Patterned Immobilization of Fluorescent Dyes on ADIBO-Coated Slides

Solutions of Oregon Green azide (13, 0.1 mM and 1 mM in PBS) or Lissamine rhodamine B azide (14, 0.1 mM) were spotted using a pipette (2 µL) on a freshly prepared dibenzocyclooctyne plate and incubated in a humidity chamber for various periods of time (vide infra). Slides were rinsed with acetone, then sonicated for 15 minutes in methanol, rinsed with acetone, and dried under a stream of nitrogen.

Patterned Immobilization of Avidin on ADIBO-Coated Slides

1 µL drops of biotin-dPEG 3+4-azide PBS solutions of different concentrations (10 mM, 1 mM, and 0.1 mM) were spotted on a ADIBO-coated glass slide. Slides were incubated in a humidity chamber for 1 hour at room temperature, rinsed with copious amounts of acetone, then water, and sonicated in DMF for 30 minutes. Slides were then immersed in a blocking solution containing 1% aminoPEG$_4$azide in DMF and incubated overnight at room temperature. The slides were then rinsed with acetone, sonicated in DMF for 30 minutes, and rinsed with distilled water, followed by immersion into a solution of avidin-FITC (50 µL of 2 g/mL in 10 mL of PBS) at 2° C. for 15 minutes. The slides were sonicated in PBS containing 0.1% Tween 20 for 30 minutes, washed with distilled water, incubated in PBS containing 0.1% of BSA for 12 hours at 2° C., sonicated again in PBS (1% of Tween 20) for 30 minutes, and rinsed with distilled water.

Patterned Immobilization of Fluorescent Probes on Azide-Coated Slides

1 µL drops of 1 mM of ADIBO-fluor (10) solution in PBS were spotted on an azide plate, followed by incubation in a humidity chamber for 12 hours at room temperature. Slides were rinsed with acetone, then sonicated for 15 minutes in methanol, rinsed with acetone, and dried under a stream of nitrogen.

For two-color derivatization, azide-coated slides patterned with ADIBO-fluor (10) spots as described above were immersed in a solution of ADIBO-Rhodamine (12, 1 mM in PBS) and incubated for 3 hours at room temperature. Slides were rinsed with acetone, then sonicated for 15 minutes in methanol, rinsed with acetone, and dried under a stream of nitrogen.

Patterned Immobilization of Avidin on Azide-Coated Slides

1 µL drops of ADIBO-biotin (8) solutions of different concentrations (10 mM, 1 mM, 0.1 mM, and 0.01 mM in PBS) were spotted on an azide-coated glass slide. Slides were incubated in a humidity chamber for 1 hour at room temperature, rinsed with copious amounts of acetone, then water, and sonicated in DMF for 30 minutes. Slides were then immersed in a blocking solution containing 0.1% ADIBO-PEG$_4$-amine (9) in DMF and incubated overnight at room temperature. The slides were rinsed with acetone, sonicated in DMF for 30 minutes, and rinsed with distilled water, followed by immersion into a solution of avidin-FITC (50 µL, of 2 mg/mL in 10 mL PBS) at 2° C. for 15 minutes. The slides were sonicated in a PBS solution containing 0.1% Tween 20 for 30 minutes, washed with distilled water, incubated in PBS containing 0.1% BSA for 12 hours at 2° C., sonicated again in PBS (1% Tween 20) for 30 minutes, and rinsed with distilled water.

Preparation of ADIBO-Coated Magnetic Beads

A solution of ADIBO-biotin conjugate (8) (25 µL, 10 mM in PBS) was added to a suspension of streptavidin-coated magnetic beads (25 µL of 10 mg/mL) in 450 µL, PBS. The resulting mixture was stirred by shaking for 2 hours at room temperature. The reaction mixture was centrifuged at 11,000 rpm for 2 minutes, the supernatant liquid was decanted, and the pellet resuspended in PBS (450 µL). The washing step was repeated two times.

Preparation of Azide-Coated Magnetic Beads

A solution of Biotin-dPEG 3+4-azide (25 µL, 10 mM in PBS) was added to a suspension of streptavidin-coated magnetic beads (25 µL of 10 mg/mL) in 450 µL PBS. The resulting mixture was stirred by shaking for 2 hours at room temperature. The reaction mixture was centrifuged at 11,000 rpm for 2 minutes, the supernatant liquid was decanted, and the pellet resuspended in PBS (450 µL, pH 7.4). The washing step was repeated two times.

Fluorescent Labelling of ADIBO-Coated Magnetic Beads

A solution of Oregon Green-azide (13) (10 mM in PBS) was added to a suspension of ADIBO-coated magnetic beads (25 µL of 10 mg/mL) and incubated for 3 hours at room temperature. Beads were centrifuged at 11,000 rpm for 1 minute, the supernatant liquid was decanted, and the pellet resuspended in 450 µL PBS containing 0.1% Tween 20, centrifuged, washed with PBS, centrifuged and resuspended in 450 µL PBS for fluorescent microscopy imaging.

Fluorescent Labelling of Azide-Coated Magnetic Beads.

A solution of ADIBO-fluor (10, 25 µL of 10 mM in PBS) was added to a suspension of azide-coated magnetic beads (25 µL of 10 mg/mL) in 450 µL PBS and incubated for 3 hours at room temperature. Beads were centrifuged at 11,000 rpm for 1 minute, the supernatant liquid was decanted, and the pellet resuspended in 450 µL PBS containing 0.1% of Tween 20, centrifuged, washed with PBS, centrifuged, and resuspended in 450 µL PBS for fluorescent microscopy imaging.

Example 2

ADIBO and Azide Functionalization of Glass Slides

Figure 3:
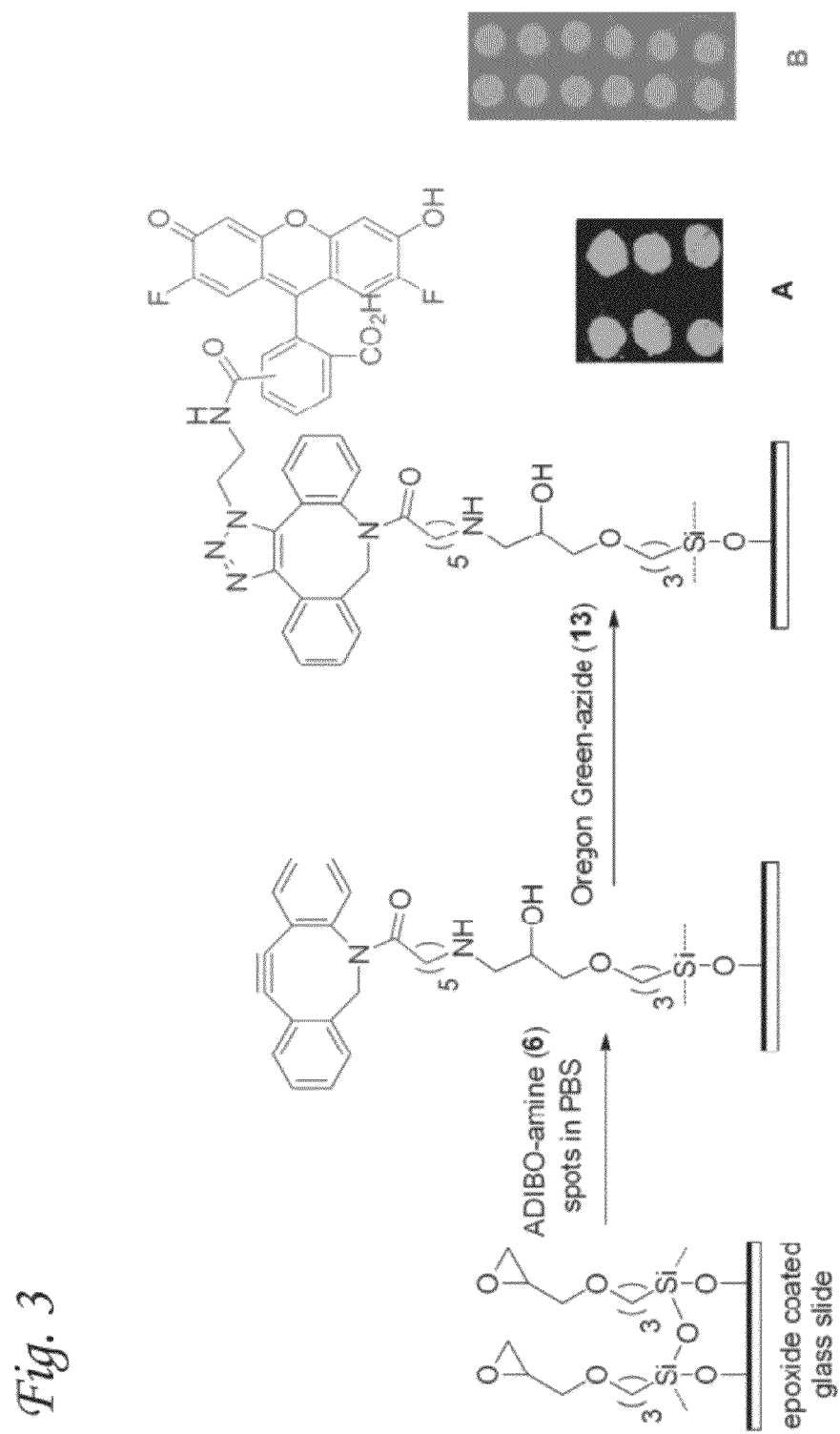
FIG. 3 is a schematic illustration of an embodiment of an exemplary ADIBO derivatization of an epoxy-coated slide followed by copper-free click immobilization of Oregon Green dye. Inserts are black and white illustrations of fluorescent images of ADIBO-slides patterned with (A) Oregon Green azide (green spots) (13), and (B) Lissamine rhodamine B azide (red spots) (14).
Figure 7:
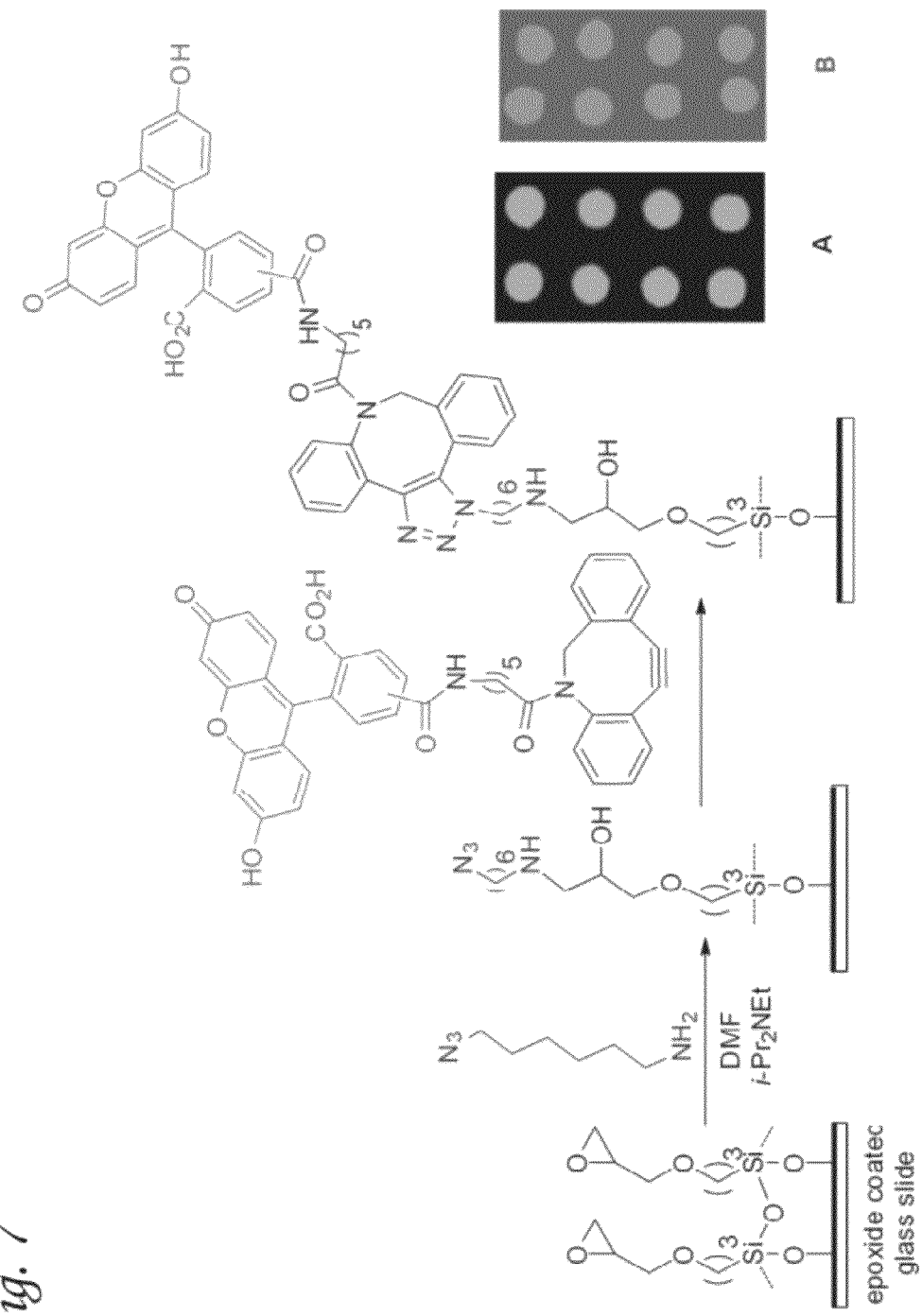
FIG. 7 is a schematic illustration of an embodiment of azide derivatization of an epoxy-coated slide followed by copper-free click immobilization of an exemplary ADIBO-OG (11). Inserts are black and white illustrations of fluorescent images of azide-slides patterned with (A) ADIBO-OG (11) (green spots) and (B) ADIBO-Rhodamine (12) (red spots).

Derivatization experiments were performed on a glass surfaces due to the ready availability, low cost, high mechanical stability, low intrinsic fluorescence, and easy surface modification techniques of the glass substrate. Freshly-prepared epoxide-coated slides were incubated in a DMF solution of ADIBO-amine 6 or 6-azidohexylamine in the presence of Hünig's base (N-ethyl-N,N-diisopropylamine) overnight, and washed with acetone, then methanol (FIGS. 3 and 7).

Oregon Green-azide (13) was used as a model compound to assess the efficiency and kinetics of the metal-free azide click immobilization on ADIBO-coated slides. To ensure that a fluorescent dye is immobilized on the slides only by the click reaction and not due physical absorption or other chemical reactions, the epoxy-coated plate was spotted with ADIBO-amine (6). After overnight incubation and washing, these plates were immersed in a PBS solution of Oregon Green azide (13, 0.01 mM) for 100 minutes and washed with acetone, then sonicated for 15 minutes in methanol, rinsed with acetone, and dried under a stream of nitrogen. The fluorescence image of the resulting slide demonstrates that dye 13 specifically binds to the ADIBO-derivatized surface and not to the rest of the slide (FIG. 3, insert A, green spots). While the value of relative fluorescence intensity (spot versus background) depends on the starting epoxy plate (VWR. Microarray Epoxy 2 Slides and Corning Epoxide Slides have also been tested), Oregon Green spots always showed bright fluorescence with 2000-6000 contrast ratio. In the following fluorescent dye patterning experiments, 2 µL drops of 0.1 mM or 0.01 mM PBS solutions of azide-dye conjugate were applied onto ADIBO-derivatized slides. Thus, 0.1 mM solution of Lissamine rhodamine B azide (14) was spotted on the ADIBO-slide, incubated for 1 hour and thoroughly washed. The fluorescence image also has a good contrast ratio (FIG. 3, insert B, red spots).

Example 3

Kinetics of Metal-Free Click Immobilization

To evaluate the kinetics of the ADIBO-azide reaction on the surface, 2 µL drops of a 0.1 mM Oregon Green azide (13) PBS solution were spotted onto ADIBO-derivatized slides.

Figure 4:
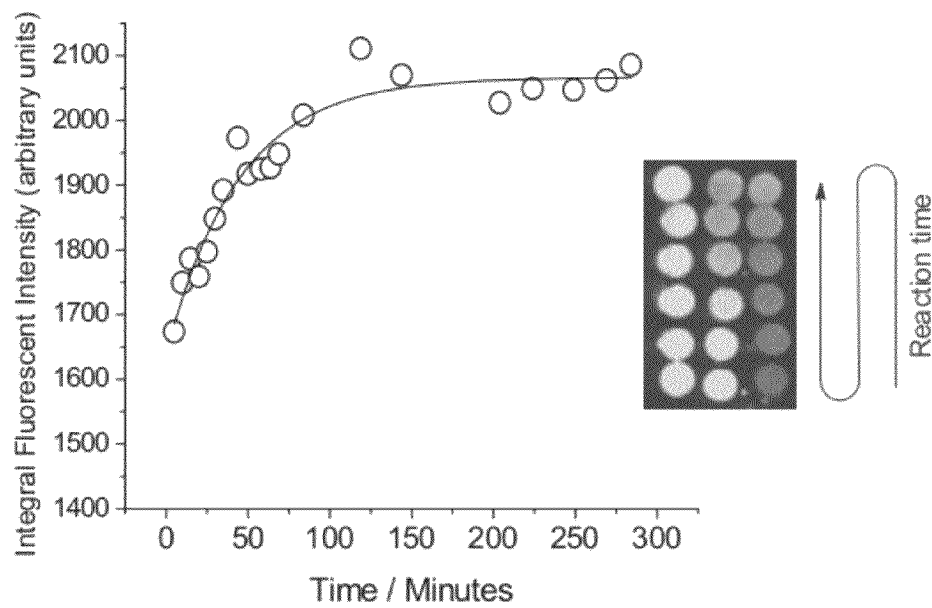
FIG. 4 is a plot illustrating the integral fluorescent intensity (y-axis; arbitrary units) of Oregon Green azide (13) spots on an ADIBO-derivatized slide versus reaction time α-axis; minutes) for an exemplary embodiment. The insert is a black and white illustration of the green spots on the slide.

The first spot was allowed to react for 284 minutes; subsequent drops were applied at different times, with the last drop applied just 5 minutes before washing. The slides were stored in a humidity chamber during this procedure. The immobilization reaction shows excellent kinetics. Within 5 minutes the relative fluorescent intensity of the green spots reaches 44-80% of the maximum value and saturation of fluorescence is achieved at approximately 100 minutes at 0.1 mM of azide (FIG. 4). As a results, incubation with the coupling reagent for 100 minutes was selected as a standard procedure for subsequent experiments.

Figure 5:
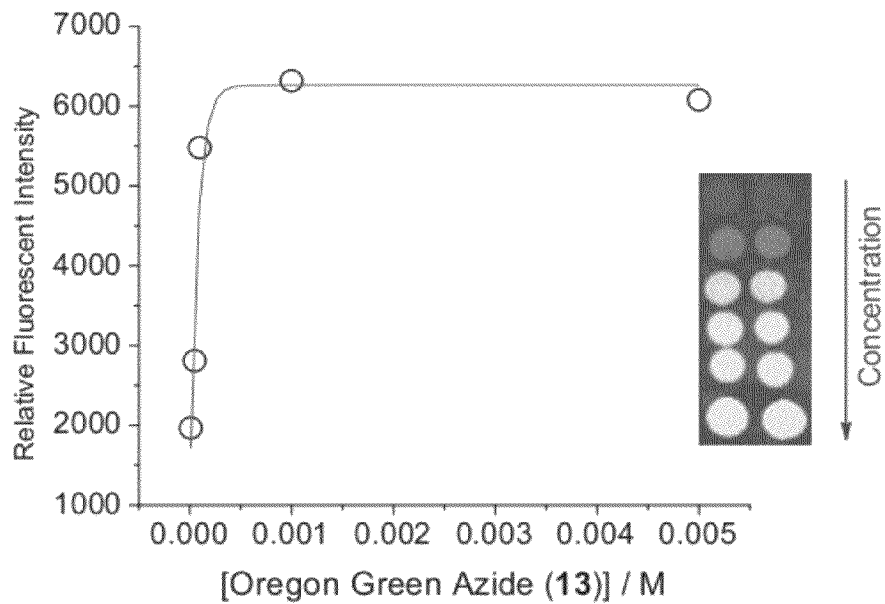
FIG. 5 is plot illustrating integral fluorescent intensity (y-axis; arbitrary units) of Oregon Green azide spots on an ADIBO-derivatized slide versus concentration α-axis; M with points at 10 µM, 50 µM, 0.1 mM, 1 mM, and 5 mM) for an exemplary embodiment. The insert is a black and white illustration of the green spots on the slide.

To optimize the concentration of the substrate for the metal-free click immobilization, an ADIBO-slide was spotted with PBS solutions of various concentration of Oregon Green azide (13): 10 μM, 50 μM, 0.1 mM, 1 mM, and 5 mM. After incubation for 100 minutes and washing, the image of the slide was recorded and the integral fluorescent intensity of the green spots analyzed (FIG. 5). The saturation of Oregon Green fluorescence is achieved around 0.1 mM concentration of the azide 13.

Example 4

Biotinylation of ADIBO-Slides and Immobilization of Avidin

Figure 6:
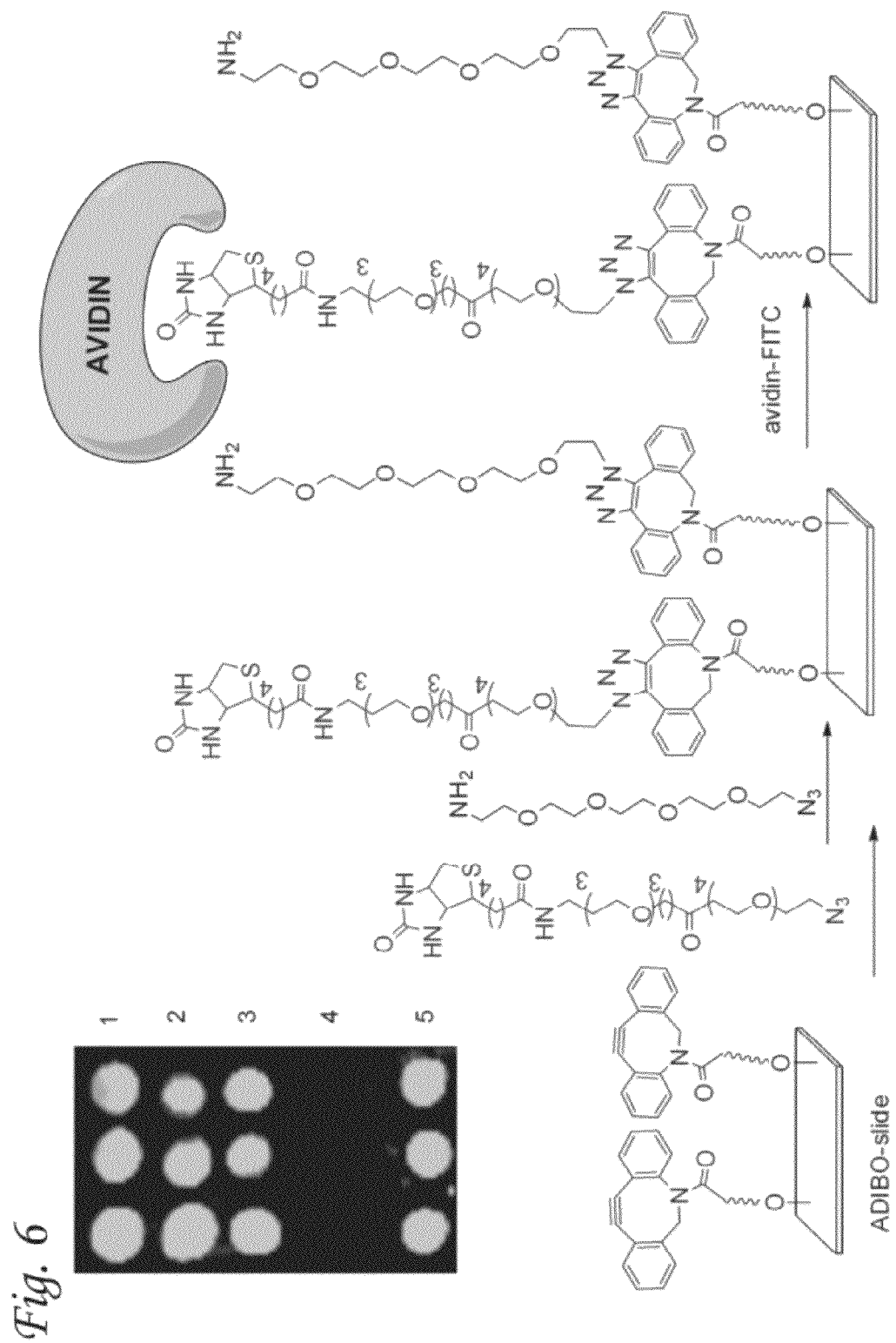
FIG. 6 is a schematic illustration of an embodiment of patterned biotinylation of an exemplary ADIBO-coated slide followed by selective immobilization of avidin-FITC. The insert is a black and white illustration of the fluorescent image of an exemplary ADIBO-slide spotted with 1 µL of the following solutions: Lane 1-3, 10 mM, 1 mM, and 0.1 mM PBS solutions of Biotin-dPEG 3+4-azide; Lane 4, 1 mM biotin-PEG$_4$-C≡CH; Lane 5, 0.1 mM of Oregon Green azide (13). The slide was then treated with aminoPEG$_4$azide and developed with avidin-FITC solution (green spots).

The exceptional selectivity and high binding constant between avidin and biotin (dissociation constant=10–15 M) (Green, *Methods Enzymol.*, 1990, 184:51-67) is widely used in bioconjugation and surface immobilization applications. See, for example, Nebhani et al., *Adv. Mat.* 2009, 21:3442-3468; Wong et al., *Chem. Rev.* 2009, 109:4025-4053; Ilia et al., *Chem. Rev.* 2009, 109:5620-5686; Ratner et al., (2004) *Biomaterials science: an introduction to materials in medicine*, Academic Press, San Diego, Calif.; Im et al, *J. Am. Chem. Soc.* 2008, 130:14424-14425; Sun et al., *Bioconjugate Chem.* 2006, 17:52-57; Jacobs et al., *Acc. Chem. Res.* 2010, 43:673-683; Wilchek et al., *Methods Enzymol.* 1990, 184:5-13; Mader et al., *Chem. Eur. J.* 2010, 16:5416-5424; Böttcher et al., *J. Am. Chem. Soc.* 2010, 132:6964-6972; Landi et al., *Org. Biomol. Chem.* 2010, 8:56-59; and Zhang et al., *Chem. Mater.* 2009, 21:4012-4018. Therefore, the efficiency of surface biotinylation using a copper-free azide click reaction was tested. As shown in FIG. 6, 1 μL drops of three different concentrations (10 mM, 1 mM, and 0.1 mM) of biotin-dPEG 3+4-azide solutions in PBS were applied onto an ADIBO-functionalized glass slide. For a comparison, 1 μL drops of a 0.1 mM PBS solution of Oregon Green azide (13) were also spotted on the slide. To test for the possibility of non-specific absorption of biotin conjugates on the ADIBO-slides, a 1 mM PBS solution of biotin-PEG$_4$-C≡CH was also spotted on the slide. After an hour-long incubation and washing, slides were immersed in a 1% DMF solution of aminoPEG$_4$azide and incubated overnight. Our initial experiment showed that dibenzocyclooctynes have significant affinity towards proteins (Mamidyala et al., *Chem. Soc. Rev.* 2010, 39:1252-1261). Exposure to the aminoPEG$_4$azide solution converts unreacted aza-dibenzocyclooctyne fragments into triazole-PEG conjugates. Patterned biotinylated slides were developed with an avidin-FITC PBS solution for 15 minutes at 2° C. and washed thoroughly. The fluorescent image of this slide (green spots) shows selective immobilization of the protein in the biotinylated areas, while non-specific binding of avidin was not observed (FIG. 6). Incubation of the avidin-FITC-patterned slides in a PBS solution containing BSA does not reduce the fluorescence, confirming the immobilization of avidin via specific biotin-avidin interactions.

Example 5

Patterning of Fluorescent Dyes on Azide-Coated Slides

To assess the efficiency of a reverse copper-free click surface derivatization, azide-coated glass slides (vide supra) were prepared. Such a surface provides a convenient platform for immobilization using both conventional (i.e., copper-catalyzed) and catalyst-free azide click reactions. 1 μL drops of a 1 mM PBS solutions of aza-dibenzocyclooctyne 6 conjugates with fluorescein (ADIBO-fluor, 10) or with Lissamine rhodamine B (ADIBO-Rhodamine, 12), were allowed to react for 12 hours, then washed thoroughly. Fluorescent images of the resulting slides with fluorescein (FIG. 7, insert A, green spots) and Lissamine rhodamine B (FIG. 7, insert B, red spots) illustrate the efficiency of substrate immobilization on the azide-derivatized surface using metal-free click chemistry.

Figure 8:
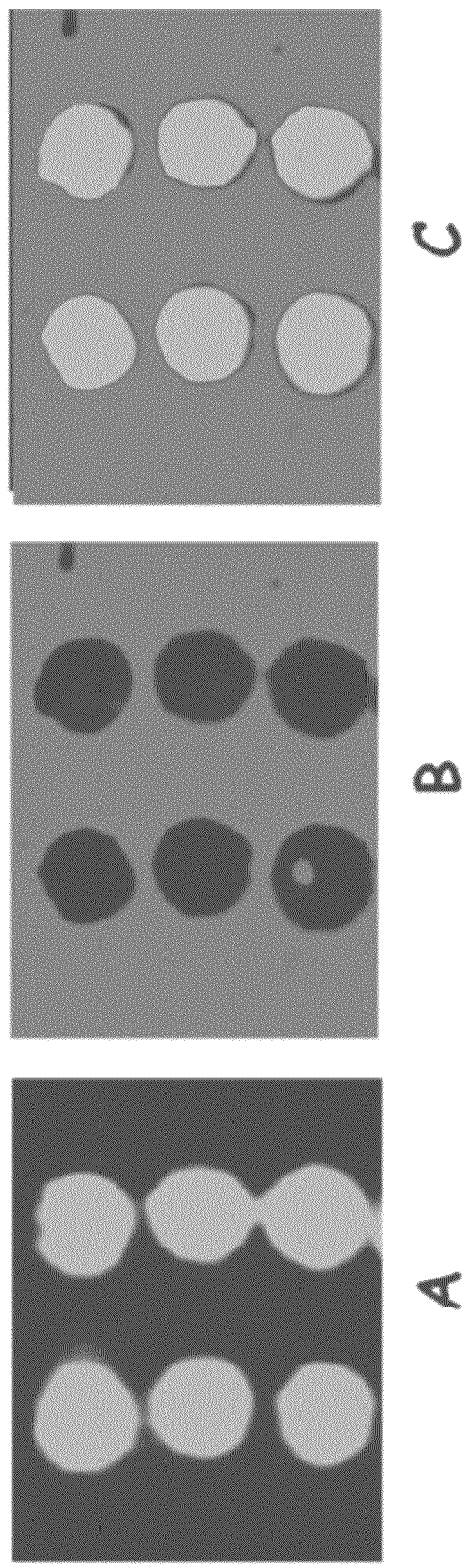
FIG. 8 is an illustration of an embodiment of two-color derivatization of azide-slides. The slide was spotted with ADIBO-fluor (10), washed and immersed in a solution of ADIBO-Rhodamine (12). The black and white illustrations represent (A) Fluorescent image recorded using 495/520 nm filter (green spots/black background); (B) image recorded using 532/580 nm filter (black spots/red background); and (C) images A and B merged (green spots/red background).

After immobilization, slides are often subjected to vigorous washing procedures, including the use of detergents and sonication in aqueous solutions and organic solvents. To test the stability of the azide surface to the washing procedures and to explore the feasibility of multi-substrate surface derivatization using copper-free click chemistry, the sequential immobilization of two fluorescent dyes was studied. The azide-coated glass slide was initially spotted with 1 μL drops of a 1 mM PBS solution of ADIBO-fluor (10) and incubated in a humidity chamber for 12 hours at room temperature. The slide was rinsed with acetone, sonicated in DMF for 30 minutes, and rinsed with distilled water, then immersed in a 0.1 mM solution of ADIBO-Rhodamine (12) for another 12 hours, then thoroughly washed. The fluorescent image recorded with a green (495-520 nm) filter clearly shows a pattern of fluorescein-immobilized green spots (FIG. 8A). The bright red background of Lissamine rhodamine B fluorescence and dark spots, where azide groups were consumed in the first step, are visible on the image recorded with a red (532-580 nm) filter (FIG. 8B). FIG. 8C shows merged images A and B (green spots/red background), which demonstrates that reactivity of an azide-derivatized surface is not significantly affected by washing procedures.

Example 6

Patterned Biotinylation of Azide-Slides and Selective Immobilization of Avidin

Figure 9:
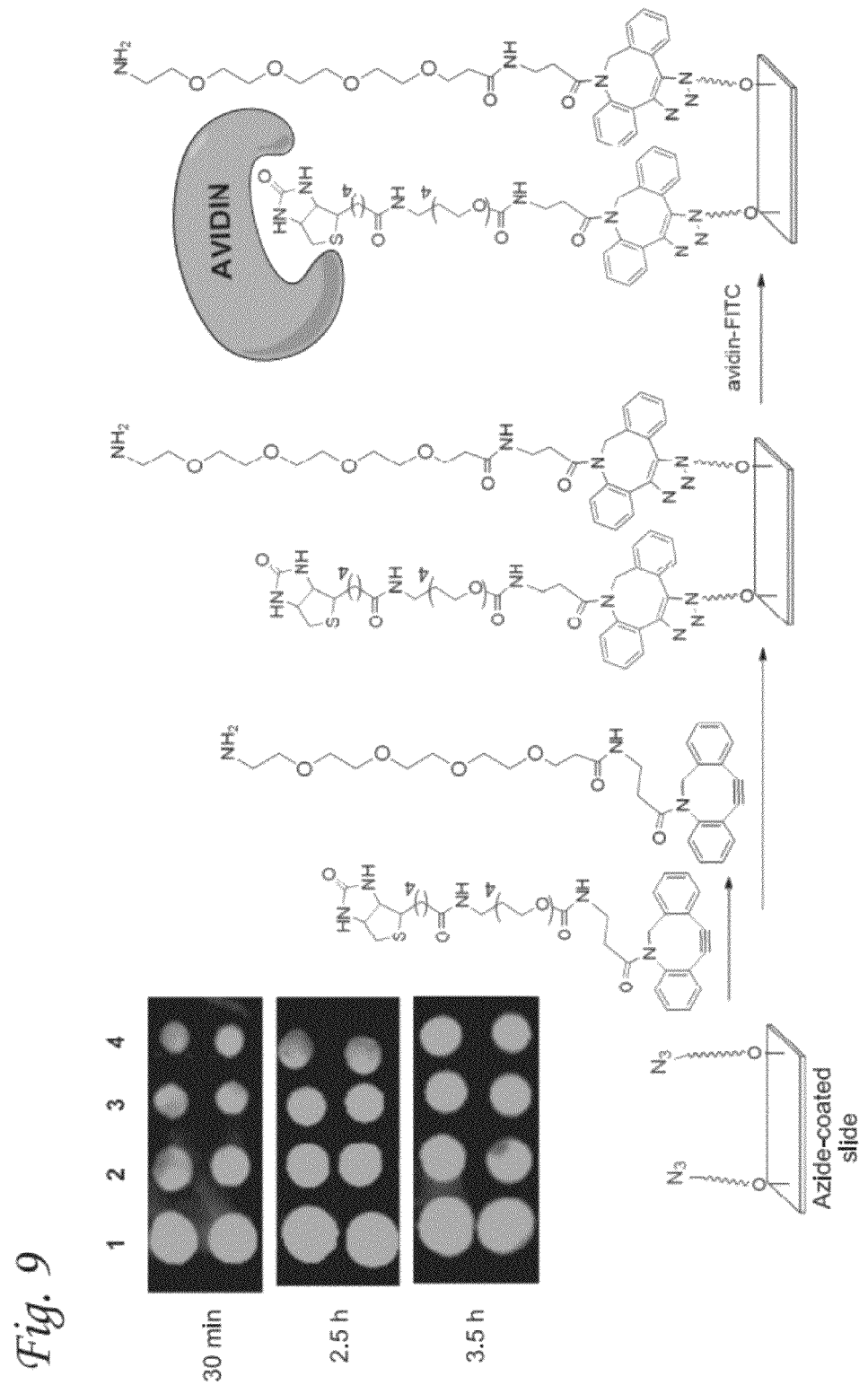
FIG. 9 is a schematic illustration of an embodiment of patterned biotinylation of azide-coated slides followed by selective immobilization of avidin-FITC. The insert is a black and white illustration of the fluorescent image of azide-derivatized slide spotted with 1 µL of ADIBO-biotin (8) solutions of the following concentration: 1) 10 mM; 2) 1 mM; 3) 0.1 mM; and 4) 0.01 mM. The first slide was incubated for 30 minutes; the second slide for 2.5 hours, and the third slide for 3.5 hours. The slides were then immersed in a solution of ADIBO-PEG$_4$-amine, and developed with a solution of avidin-FITC (green spots).

To further demonstrate the versatility of the copper-free click reaction for protein immobilization, patterned biotinylation of azide-derivatized slides was conducted, followed by the immobilization of avidin. Azide-functionalized glass slides was spotted with 1 μL drops of four different concentrations (10 mM, 1 mM, 0.1 mM, and 0.01 mM) of a PBS solution of ADIBO-biotin (8). Slides were incubated in a humidity chamber for 30 minutes, 2.5 hours, and 3.5 hours and washed with copious amounts of acetone, then water, and sonicated in DMF. To reduce nonspecific binding of the protein, slides were immersed in a blocking solution containing 0.1% ADIBO-PEG$_4$-amine (9) in DMF and kept overnight. The slides were then washed, incubated in a solution of avidin-FITC at 2° C. for 15 minutes, and washed again. As in the case of patterned biotinylation of ADIBO-slides, fluorescent images show selective immobilization of the fluorescently labeled protein in biotinylated areas. No significant non-specific binding of avidin to the slides was observed (FIG. 9). Fluorescent intensity of the spots produced at various concentrations of ADIBO-biotin and incubation time illustrate the efficiency of the reaction. Even at 10 µM concentration of ADIBO-biotin (8), a 30 minutes incubation produces a brightly fluorescent spot after avidin-FTIC development.

Example 7

Catalyst-Free Derivatization of Microbeads

Figure 10:
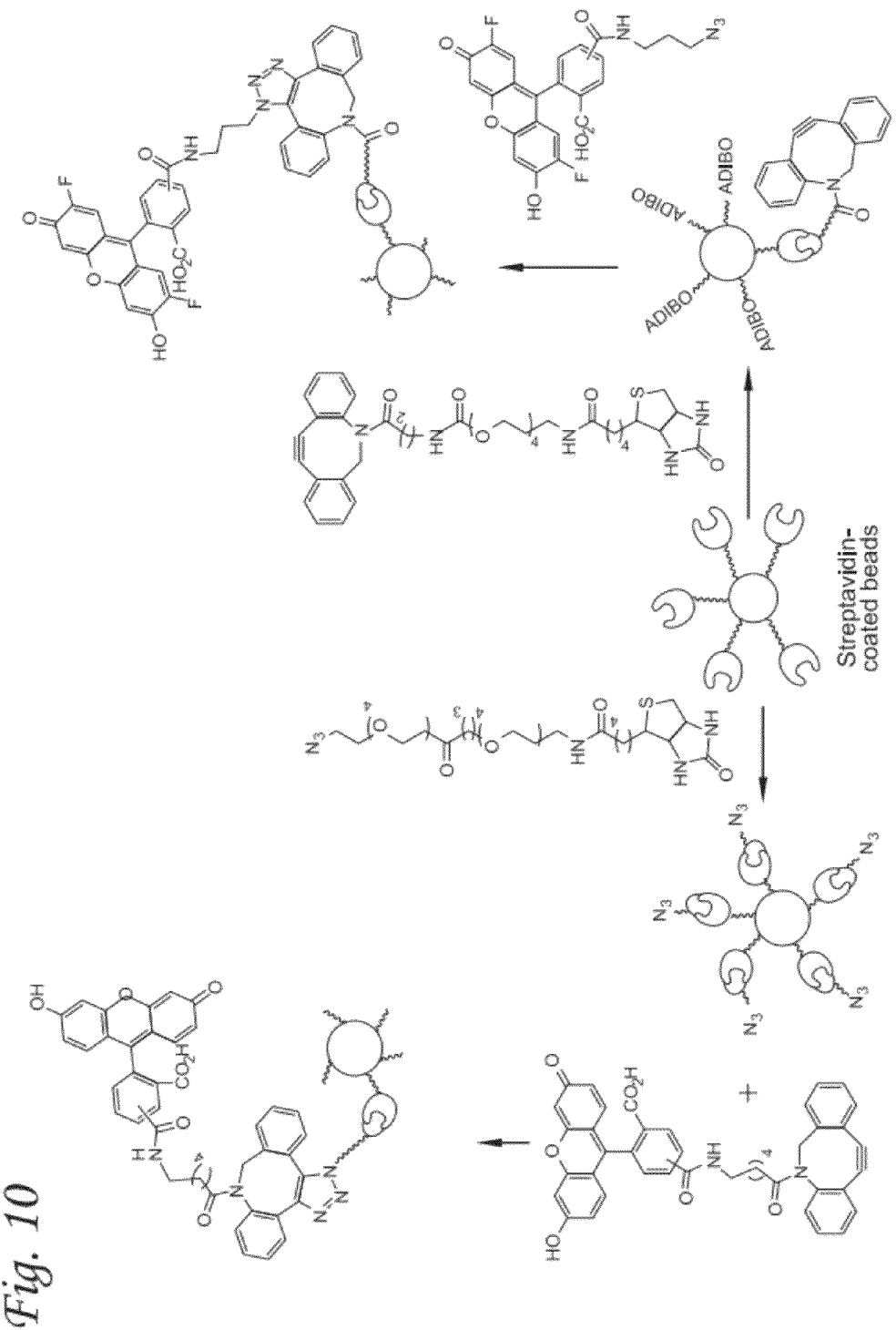
FIG. 10 is a schematic illustration of embodiments of derivatization of streptavidin-coated magnetic beads with azide and aza-dibenzocyclooctynes, followed by the metal-free azide click coupling to fluorescent dyes.

To demonstrate the utility of the copper-free azide click reaction for the modification of microparticle surfaces, the application of this reaction to the fluorescent labeling of streptavidin-coated magnetic beads was explored. The surface of the beads was derivatized with azide groups by treating a suspension of the beads with biotin-dPEG 3+4-azide (FIG. 10). The aza-dibenzocyclooctyne functionalization of streptavidin beads was achieved by reacting the Bonner with ADIBO-biotin (8, FIG. 10).

Figure 11:
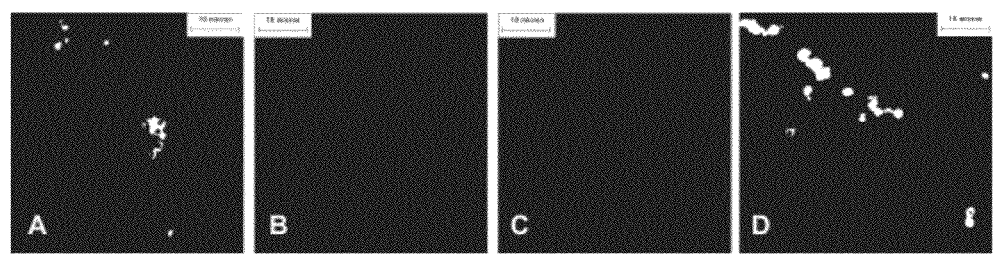
FIG. 11 is a black and white illustration of fluorescent confocal microscope images (green portions appear white) of exemplary PBS suspensions of streptavidin-coated magnetic beads: (A) treated with ADIBO-biotin (8) followed by reaction with Oregon Green azide (13); (B) treated with biotin-PEG$_4$-C≡CH and then with Oregon Green azide (13); (C) incubated with ADIBO-fluor only (10); and (D) treated with biotin-dPEG 3+4-azide and then with incubated ADIBO-fluor (10).
Figure 12:
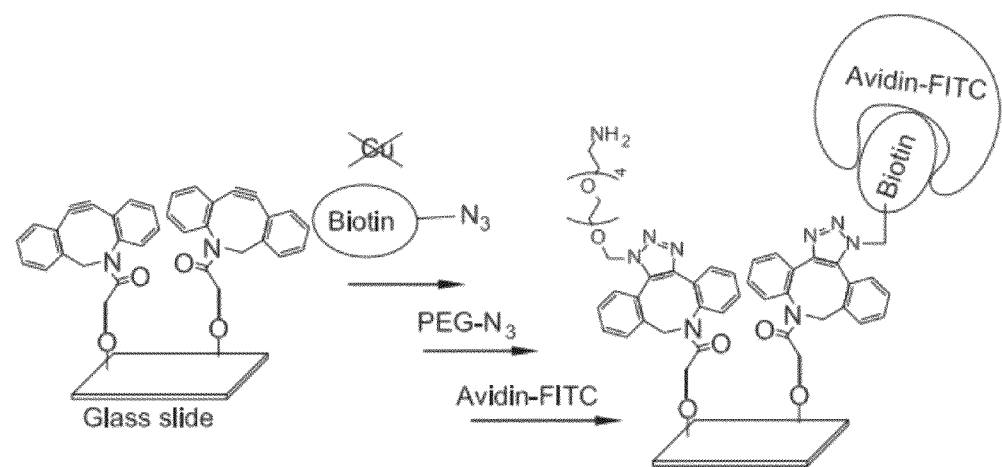
FIG. 12 is a schematic illustration showing ADIBO derivatized glass slides and/or microbeads, which can allow for the efficient immobilization of azide-labeled biomolecules. The alternative procedure which uses azide-derivatized surfaces for the attachment of ADIBO-conjugated substrates is equally effective. Both techniques show excellent kinetics under ambient conditions and do not require any catalysts. PEGylation of the surfaces using copper-free ADIBO-azide click reaction can significantly reduce non-specific binding of proteins.

The ADIBO-functionalized streptavidin beads were suspended in a PBS solution of Oregon Green azide (13) and incubated for 3 hours at room temperature. Beads were washed and resuspended in PBS for imaging via fluorescent confocal microscopy. FIG. 11A shows the bright green fluorescence of these Oregon Green-labeled beads. The starting (unmodified) streptavidin magnetic beads treated with 13 under the same conditions show no detectable emission. As an additional control experiment, the beads were derivatized with terminal acetylene groups by treating streptavidin beads with biotin-PEG$_4$-C≡CH. Incubation of the resulting particles in an Oregon Green azide (13) solution, followed by thorough washing, did not induce detectable fluorescence in the beads (FIG. 11B), Magnetic streptavidin beads directly treated with ADIBO-fluor (10) showed no fluorescence (FIG. 11C). Azide-derivatized microbeads were labeled with fluorescein by reacting them with an ADIBO-fluorescein conjugate (10, FIG. 11D).

In conclusion, an efficient synthesis of aza-dibenzocyclooctynes (ADIBO) starting from inexpensive precursors has been disclosed. This method allows for preparation of ADIBO derivatives on a large scale. The utility and excellent kinetics of catalyst-free ADIBO-azide cycloaddition for the patterned derivatization of glass slides and streptavidin beads has been demonstrated. The same metal-free click reaction was employed for the PEGylation of unfunctionalized areas of the surface. Such treatment allowed for dramatic reduction or complete elimination of non-specific binding of proteins to the surface. The strategy described in this report provides a convenient tool for the site-specific covalent immobilization of various biomolecules. These procedures can be especially useful in cases where presence of copper ions has to be avoided.

The complete disclosure of all patents, patent applications, and publications, and electronically available material (e.g., GenBank amino acid and nucleotide sequence submissions; and protein data bank (pdb) submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:
1. An alkyne of the formula:

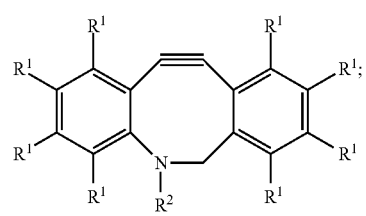

Formula II wherein:
each $R^1$ independently represents H or an organic group; and
$R^2$ represents a —C(O)—$R^4$ group, wherein $R^4$ represents an organic group attached to a glass slide or a particle surface.

2. The alkyne of claim 1 wherein each $R^1$ is hydrogen.

3. The alkyne of claim 1 wherein $R^4$ is attached to the glass slide or the particle surface by hydrogen bonding and/or covalent bonding.

4. A method of preparing a heterocyclic compound, the method comprising:
combining at least one azide of the formula $R^3$—$N_3$ with at least one alkyne according to claim 1; and
allowing the at least one azide and the at least one alkyne to react under conditions effective to form a heterocyclic compound of one or more of the following formulas:

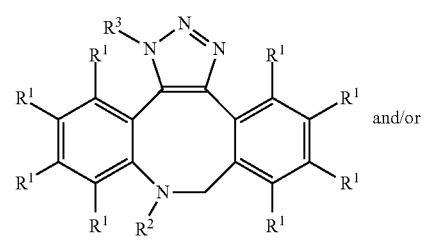

Formula III and/or

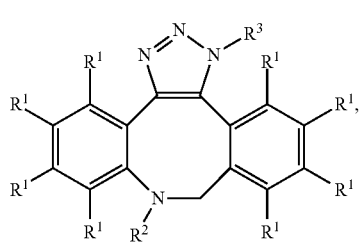

Formula IV wherein:
each $R^1$ independently represents H or an organic group;
$R^2$ represents a —C(O)—$R^4$ group;
$R^3$ represents an organic group; and
$R^4$ represents an organic group attached to a glass slide or a particle surface.

5. The method of claim 4 wherein conditions effective to form the heterocyclic compound include the substantial absence of added catalyst.

6. The method of claim 4 wherein $R^3$ comprises a detectable label, and the method comprises labeling the solid surface.

7. The method of claim 6 wherein the detectable label is an affinity label.

8. A method of preparing a heterocyclic alkyne, the method comprising:
subjecting a compound of the formula:

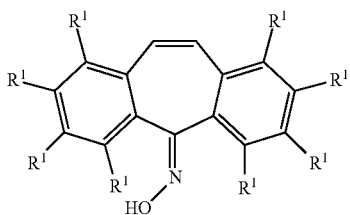

Formula V to conditions effective for a Beckman rearrangement to provide a lactam of the formula:

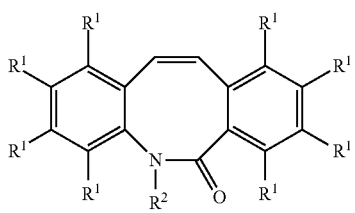

Formula VI wherein each $R^1$ independently represents H or an organic group, and $R^2$ is H;

subjecting the lactam of Formula VI to conditions effective to reduce the lactam and provide a heterocyclic alkene of the formula:

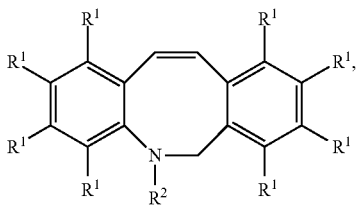

Formula I wherein each $R^1$ independently represents H or an organic group, and $R^2$ is H;

converting $R^2$ from H to a —C(O)—$R^4$ group, wherein $R^4$ represents an organic group; and subjecting the converted heterocyclic alkene to conditions effective to convert the alkene to an alkyne of the formula:

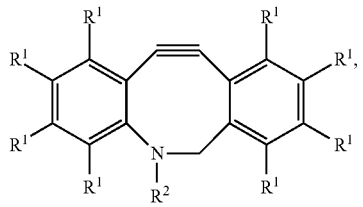

Formula II wherein each $R^1$ independently represents H or an organic group; $R^2$ represents a —C(O)—$R^4$ group; and $R^4$ represents an organic group.

9. The method of claim 8 wherein each $R^1$ represents H.

10. The method of claim 8 wherein conditions effective for the Beckman rearrangement comprise treatment with polyphosphoric acid at a temperature of 25° C. to 200° C.

11. The method of claim 8 wherein conditions effective to reduce the lactam comprise treatment with lithium aluminum hydride under anhydrous conditions.

12. The method of claim 11 wherein anhydrous conditions comprise the presence of an aprotic solvent.

13. The method of claim 8 wherein conditions effective to convert the alkene to the alkyne comprise:

halogenating the alkene to form a dihalide; and dehydrohalogenating the dihalide to form the alkyne.

14. The method of claim 13 wherein the halogen comprises bromine.

15. An alkyne of the formula:

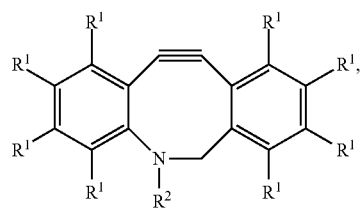

Formula II wherein:

each $R^1$ independently represents H or a C1-C12 hydrocarbon moiety; and $R^2$ represents a —C(O)—$R^4$ group, wherein $R^4$ represents a linking group attached to a glass slide or a particle surface.

16. The method of claim 4, wherein each $R^1$ independently represents H or a C1-C12 hydrocarbon moiety.

17. The method of claim 8, wherein each $R^1$ independently represents H or a C1-C12 hydrocarbon moiety; and $R^4$ represents a detectable label or a linking group.

* * * * *